(12) United States Patent
Newell et al.

(10) Patent No.: US 11,938,056 B2
(45) Date of Patent: Mar. 26, 2024

(54) METHODS AND DEVICES FOR HANDLING A FLUID AND DELIVERING THE FLUID TO THE EYE

(71) Applicant: Eyenovia, Inc., New York, NY (US)

(72) Inventors: Matthew Newell, Reno, NV (US); Luke Clauson, Reno, NV (US); Nicholas Lewis, Reno, NV (US); Michael Raye, Reno, NV (US)

(73) Assignee: Eyenovia, Inc., New York, NY (US)

( * ) Notice: Subject to any disclaimer, the term of this patent is extended or adjusted under 35 U.S.C. 154(b) by 1011 days.

(21) Appl. No.: 16/621,564

(22) PCT Filed: Jun. 11, 2018

(86) PCT No.: PCT/US2018/036908
§ 371 (c)(1),
(2) Date: Dec. 11, 2019

(87) PCT Pub. No.: WO2018/227190
PCT Pub. Date: Dec. 13, 2018

(65) Prior Publication Data
US 2020/0197218 A1   Jun. 25, 2020

Related U.S. Application Data

(60) Provisional application No. 62/517,914, filed on Jun. 10, 2017.

(51) Int. Cl.
*A61F 9/00* (2006.01)
*A61M 11/00* (2006.01)

(52) U.S. Cl.
CPC ......... *A61F 9/0008* (2013.01); *A61M 11/005* (2013.01); *A61M 2205/123* (2013.01);
(Continued)

(58) Field of Classification Search
CPC ............ B05B 17/0646; A61F 9/00745; A61M 11/006
See application file for complete search history.

(56) References Cited

U.S. PATENT DOCUMENTS

| 558,866 A | 4/1896 | Vaughn |
|---|---|---|
| 1,482,747 A | 2/1924 | Howe |

(Continued)

FOREIGN PATENT DOCUMENTS

| CA | 2873582 A1 | 11/2012 |
|---|---|---|
| CN | 203609747 U | 5/2014 |

(Continued)

OTHER PUBLICATIONS

"Alcon. RTM: Sharing One Vision," 2009 Annual Report, 46 pages, (2009).

(Continued)

*Primary Examiner* — Courtney B Fredrickson
(74) *Attorney, Agent, or Firm* — Mintz Levin Cohn Ferris Glovsky and Popeo, P.C.

(57) ABSTRACT

Methods and devices for handling a fluid and delivering the fluid to the eye. The device has a vibrating element with a plurality of openings through which a fluid is ejected when the vibrated. An enclosure defines a chamber which holds a single application of the fluid. The enclosure may be biased against the vibrating element with a spring load developed in whole or part by the resilient structure of the enclosure. The chamber may be substantially empty after the single application.

57 Claims, 30 Drawing Sheets

(52) U.S. Cl.
CPC ............... *A61M 2205/3306* (2013.01); *A61M 2205/3317* (2013.01); *A61M 2205/8206* (2013.01); *A61M 2210/0612* (2013.01)

(56) References Cited

U.S. PATENT DOCUMENTS

| | | | |
|---|---|---|---|
| 1,493,410 A | 5/1924 | Wolcott |
| 1,799,529 A | 4/1931 | Poetsch |
| 1,988,637 A | 1/1935 | Tinkham |
| 2,189,643 A | 2/1940 | Ward |
| 2,200,008 A | 5/1940 | Nowak |
| 2,249,608 A | 7/1941 | Greene |
| 2,322,808 A | 6/1943 | Hothersall |
| 2,552,857 A | 5/1951 | Knapp |
| 2,595,317 A | 5/1952 | White, Jr. |
| 2,698,619 A | 1/1955 | Beacham et al. |
| 2,987,439 A | 6/1961 | Wittlinger |
| 3,170,462 A | 2/1965 | Hall |
| 3,187,757 A | 6/1965 | Jones et al. |
| 3,237,809 A | 3/1966 | Daragan et al. |
| 3,310,830 A | 3/1967 | Gattone |
| 3,314,426 A | 4/1967 | Carroll |
| 3,439,674 A | 4/1969 | Lelicoff |
| 3,602,399 A | 8/1971 | Litman et al. |
| 3,658,257 A | 4/1972 | Rood |
| 3,709,235 A | 1/1973 | Washburn et al. |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,892,235 A | 7/1975 | Van Amerongen et al. |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,012,798 A | 3/1977 | Liautaud |
| 4,052,985 A | 10/1977 | Coleman et al. |
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,533,082 A | 8/1985 | Maehara et al. |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,691,885 A | 9/1987 | Lawrance |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikstrom |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |
| 5,171,306 A | 12/1992 | Vo |
| 5,176,856 A | 1/1993 | Takahashi et al. |
| 5,193,745 A | 3/1993 | Holm |
| 5,200,248 A | 4/1993 | Thompson et al. |
| 5,201,726 A | 4/1993 | Kirkham |
| 5,203,506 A | 4/1993 | Gross et al. |
| 5,226,538 A | 7/1993 | Roselle |
| 5,247,842 A | 9/1993 | Kaufman et al. |

(56) References Cited

U.S. PATENT DOCUMENTS

| | | |
|---|---|---|
| 5,252,318 A | 10/1993 | Joshi et al. |
| 5,256,157 A | 10/1993 | Samiotes et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,296,673 A | 3/1994 | Smith |
| 5,299,739 A | 4/1994 | Takahashi et al. |
| 5,312,046 A | 5/1994 | Knoch et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,497,944 A | 3/1996 | Weston et al. |
| 5,499,751 A | 3/1996 | Meyer |
| D368,774 S | 4/1996 | Py |
| 5,511,726 A | 4/1996 | Greenspan et al. |
| 5,515,841 A | 5/1996 | Robertson et al. |
| 5,518,179 A | 5/1996 | Humberstone et al. |
| 5,522,385 A | 6/1996 | Lloyd et al. |
| 5,529,055 A | 6/1996 | Gueret |
| 5,551,416 A | 9/1996 | Stimpson et al. |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,688,232 A | 11/1997 | Flower |
| 5,693,016 A | 12/1997 | Gumaste et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,855,564 A | 1/1999 | Ruskewicz |
| 5,881,716 A | 3/1999 | Wirch et al. |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| 5,938,637 A * | 8/1999 | Austin ............... A61M 5/50 604/141 |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,000,394 A | 12/1999 | Blaha-Schnabel et al. |
| 6,008,468 A | 12/1999 | Tanaka et al. |
| 6,011,062 A | 1/2000 | Schneider et al. |
| 6,014,970 A | 1/2000 | Ivri et al. |
| 6,027,450 A | 2/2000 | Brown et al. |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,116,893 A | 9/2000 | Peach |
| 6,135,427 A | 10/2000 | Tsai |
| 6,152,383 A | 11/2000 | Chen |
| 6,158,431 A | 12/2000 | Poole |
| 6,159,188 A | 12/2000 | Laibovitz et al. |
| 6,171,276 B1 | 1/2001 | Lippe et al. |
| 6,193,683 B1 | 2/2001 | Ludin et al. |
| 6,196,219 B1 | 3/2001 | Hess et al. |
| 6,203,759 B1 | 3/2001 | Pelc et al. |
| 6,205,999 B1 | 3/2001 | Ivri et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,235,177 B1 | 5/2001 | Borland et al. |
| 6,251,952 B1 | 6/2001 | Siff |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,297,289 B2 | 10/2001 | Siff |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,397,838 B1 | 6/2002 | Zimlich, Jr. et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,435,175 B1 | 8/2002 | Stenzler |
| 6,442,423 B1 | 8/2002 | Domb et al. |
| 6,443,146 B1 | 9/2002 | Voges |
| 6,467,476 B1 | 10/2002 | Ivri et al. |
| 6,513,682 B1 | 2/2003 | Cohen et al. |
| 6,524,287 B1 | 2/2003 | Cogger |
| 6,526,976 B1 | 3/2003 | Baran |
| 6,530,370 B1 | 3/2003 | Heinonen |
| 6,537,817 B1 | 3/2003 | Papen |
| RE38,077 E | 4/2003 | Cohen et al. |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,547,755 B1 | 4/2003 | Lippe et al. |
| 6,547,770 B2 | 4/2003 | Carlsson et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,581 B1 | 8/2003 | Babaev |
| 6,610,033 B1 | 8/2003 | Melanson et al. |
| 6,610,036 B2 | 8/2003 | Branch et al. |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,651,844 B2 | 11/2003 | Tomaka et al. |
| 6,659,364 B1 | 12/2003 | Humberstone et al. |
| 6,660,249 B2 | 12/2003 | Montgomery |

(56) References Cited

U.S. PATENT DOCUMENTS

| | | |
|---|---|---|
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | DellaVecchia et al. |
| 6,755,189 B2 | 6/2004 | Ivri et al. |
| 6,761,286 B2 | 7/2004 | Py et al. |
| 6,776,309 B2 | 8/2004 | Schultz |
| 6,782,886 B2 | 8/2004 | Narayan et al. |
| 6,789,741 B2 | 9/2004 | Varanasi et al. |
| 6,814,071 B2 | 11/2004 | Klimowicz et al. |
| 6,830,046 B2 | 12/2004 | Blakley et al. |
| 6,845,770 B2 | 1/2005 | Klimowicz et al. |
| 6,851,626 B2 | 2/2005 | Patel et al. |
| 6,854,461 B2 | 2/2005 | Nichols et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,886,556 B2 | 5/2005 | Fuchs |
| 6,889,690 B2 | 5/2005 | Crowder et al. |
| 6,901,926 B2 | 6/2005 | Yamamoto et al. |
| 6,913,205 B2 | 7/2005 | Cornet et al. |
| 6,915,962 B2 | 7/2005 | Power et al. |
| 6,921,020 B2 | 7/2005 | Ivri |
| 6,926,208 B2 | 8/2005 | Ivri |
| 6,946,117 B1 | 9/2005 | Schutt et al. |
| 6,948,491 B2 | 9/2005 | Loeffler et al. |
| 6,964,647 B1 | 11/2005 | Babaev |
| 6,968,840 B2 | 11/2005 | Smith et al. |
| 6,969,165 B2 | 11/2005 | Olsen |
| 6,971,383 B2 | 12/2005 | Hickey et al. |
| 6,974,450 B2 | 12/2005 | Weber et al. |
| 6,976,279 B1 | 12/2005 | Berke et al. |
| 6,976,969 B2 | 12/2005 | Messerly |
| 6,978,941 B2 | 12/2005 | Litherland et al. |
| 6,978,945 B2 | 12/2005 | Wong et al. |
| 6,991,137 B2 | 1/2006 | Schultz |
| 7,014,068 B1 | 3/2006 | Cohen et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,070,071 B2 | 7/2006 | Pavlu et al. |
| 7,073,733 B2 | 7/2006 | Cohen et al. |
| 7,081,757 B2 | 7/2006 | Unsworth et al. |
| 7,083,112 B2 | 8/2006 | Ivri |
| 7,100,600 B2 | 9/2006 | Loeffler et al. |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,195,011 B2 | 3/2007 | Loeffler et al. |
| 7,201,167 B2 | 4/2007 | Fink et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,261,224 B2 | 8/2007 | Cohen et al. |
| 7,267,121 B2 | 9/2007 | Ivri |
| 7,290,541 B2 | 11/2007 | Ivri et al. |
| 7,314,187 B2 | 1/2008 | Hochrainer et al. |
| 7,316,067 B2 | 1/2008 | Blakey |
| 7,322,349 B2 | 1/2008 | Power |
| 7,331,339 B2 | 2/2008 | Smith et al. |
| 7,357,133 B2 | 4/2008 | Goodchild |
| 7,360,536 B2 | 4/2008 | Patel et al. |
| 7,442,180 B2 | 10/2008 | Vitello et al. |
| 7,448,559 B2 | 11/2008 | Le Maner et al. |
| 7,455,393 B2 | 11/2008 | Onozawa |
| 7,469,874 B2 | 12/2008 | Akahori |
| 7,472,701 B2 | 1/2009 | Pfichner et al. |
| 7,524,006 B2 | 4/2009 | Shin et al. |
| D597,206 S | 7/2009 | Collins, Jr. et al. |
| 7,574,787 B2 | 8/2009 | Xu et al. |
| 7,600,511 B2 | 10/2009 | Power et al. |
| 7,628,339 B2 | 12/2009 | Ivri et al. |
| 7,651,011 B2 | 1/2010 | Cohen et al. |
| 7,677,467 B2 * | 3/2010 | Fink ............... A61M 15/0068 239/338 |
| 7,678,089 B2 | 3/2010 | Py et al. |
| 7,712,466 B2 | 5/2010 | Addington et al. |
| 7,752,058 B2 | 7/2010 | Sasaki et al. |
| 7,819,115 B2 | 10/2010 | Sexton et al. |
| 7,849,851 B2 | 12/2010 | Zierenberg et al. |
| 7,856,975 B2 | 12/2010 | Nobutani et al. |
| 7,883,031 B2 | 2/2011 | Collins, Jr. et al. |
| 7,891,580 B2 | 2/2011 | Valpey, III et al. |
| 7,900,850 B2 | 3/2011 | Zengerle et al. |
| 7,946,291 B2 | 5/2011 | Fink et al. |
| 7,954,486 B2 | 6/2011 | Papania et al. |
| 7,954,730 B2 | 6/2011 | Ng |
| 7,971,588 B2 | 7/2011 | Fink et al. |
| 7,981,097 B2 | 7/2011 | Paoli, Jr. |
| 8,128,606 B2 | 3/2012 | Anderson et al. |
| 8,163,257 B2 | 4/2012 | Wallace et al. |
| 8,205,971 B2 | 6/2012 | Newton et al. |
| 8,246,589 B2 | 8/2012 | Marx |
| 8,267,285 B2 | 9/2012 | Cohen et al. |
| 8,342,368 B2 | 1/2013 | Ophardt et al. |
| 8,348,177 B2 | 1/2013 | Loverich et al. |
| 8,376,525 B2 | 2/2013 | Asai et al. |
| 8,387,834 B2 | 3/2013 | Proper et al. |
| 8,485,503 B2 | 7/2013 | Lei |
| 8,545,463 B2 | 10/2013 | Collins, Jr. et al. |
| 8,556,132 B2 | 10/2013 | Cohen et al. |
| 8,561,604 B2 | 10/2013 | Ivri et al. |
| 8,578,931 B2 | 11/2013 | Ivri et al. |
| 8,616,195 B2 | 12/2013 | Power et al. |
| 8,734,408 B2 | 5/2014 | Marx |
| 8,936,021 B2 | 1/2015 | Collins, Jr. |
| 8,950,394 B2 | 2/2015 | Patton et al. |
| 9,004,061 B2 | 4/2015 | Patton et al. |
| 9,022,970 B2 | 5/2015 | Dacquay et al. |
| 9,039,666 B2 | 5/2015 | Voss et al. |
| 9,050,424 B2 | 6/2015 | Van Der Mark |
| 9,068,566 B2 | 6/2015 | Ivri |
| 9,108,211 B2 | 8/2015 | Ivri |
| 9,180,261 B2 | 11/2015 | Patton et al. |
| 9,186,690 B2 | 11/2015 | Scanlon et al. |
| 9,279,177 B2 | 3/2016 | Choi et al. |
| 9,333,523 B2 | 5/2016 | Lowy |
| 9,421,199 B2 | 8/2016 | Ostrow et al. |
| 9,463,486 B2 | 10/2016 | Wilkerson et al. |
| 9,545,488 B2 | 1/2017 | Patton et al. |
| 9,610,192 B2 | 4/2017 | Marx |
| 9,623,174 B2 | 4/2017 | Pang et al. |
| 9,801,757 B2 | 10/2017 | Voss et al. |
| 10,251,875 B2 | 4/2019 | Puri et al. |
| 10,265,216 B2 | 4/2019 | Nielsen |
| 10,583,132 B2 | 3/2020 | Puri et al. |
| 10,624,781 B2 | 4/2020 | Ivri |
| 10,751,214 B2 | 8/2020 | Kelly |
| 10,842,787 B2 | 11/2020 | Ostrow et al. |
| 10,888,454 B2 | 1/2021 | Ivri et al. |
| 10,888,557 B2 | 1/2021 | Ostrow et al. |
| 10,940,145 B2 | 3/2021 | Ostrow et al. |
| 10,953,002 B2 | 3/2021 | Ostrow et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |

(56) References Cited

U.S. PATENT DOCUMENTS

| | | |
|---|---|---|
| 2002/0043262 A1 | 4/2002 | Langford et al. |
| 2002/0074362 A1 | 6/2002 | Py et al. |
| 2002/0085067 A1 | 7/2002 | Palifka et al. |
| 2002/0104530 A1 | 8/2002 | Ivri et al. |
| 2002/0121285 A1 | 9/2002 | Poniatowski et al. |
| 2002/0124843 A1 | 9/2002 | Skiba et al. |
| 2002/0158196 A1 | 10/2002 | Berggren et al. |
| 2002/0161344 A1 | 10/2002 | Peclat et al. |
| 2003/0024526 A1 | 2/2003 | Ganan-Calvo |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0055595 A1 | 3/2004 | Noymer et al. |
| 2004/0082884 A1 | 4/2004 | Pal et al. |
| 2004/0092548 A1 | 5/2004 | Embleton et al. |
| 2004/0116524 A1 | 6/2004 | Cohen et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0215157 A1 | 10/2004 | Peclat et al. |
| 2004/0220537 A1 | 11/2004 | Embleton et al. |
| 2004/0256487 A1 | 12/2004 | Collins et al. |
| 2005/0029307 A1 | 2/2005 | Py et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0205089 A1 | 9/2005 | Fink et al. |
| 2005/0240162 A1 | 10/2005 | Chen et al. |
| 2005/0244339 A1 | 11/2005 | Jauernig et al. |
| 2005/0260203 A1 | 11/2005 | Wiegand et al. |
| 2005/0261641 A1 | 11/2005 | Warchol et al. |
| 2005/0263149 A1 | 12/2005 | Noymer et al. |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0028420 A1 | 2/2006 | Nagata et al. |
| 2006/0039715 A1 | 2/2006 | Rimai et al. |
| 2006/0041248 A1 | 2/2006 | Patton et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0219806 A1 | 10/2006 | Wang et al. |
| 2006/0243820 A1 | 11/2006 | Ng |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1* | 5/2007 | Collins, Jr. ......... A61M 11/065 239/102.1 |
| 2007/0119969 A1 | 5/2007 | Collins et al. |
| 2007/0211212 A1 | 9/2007 | Bennwik |
| 2007/0248645 A1 | 10/2007 | Bague et al. |
| 2007/0270768 A1 | 11/2007 | Dacquay et al. |
| 2008/0017189 A1 | 1/2008 | Ruckdeschel et al. |
| 2008/0043061 A1 | 2/2008 | Glezer et al. |
| 2008/0142624 A1 | 6/2008 | Ivri et al. |
| 2008/0164339 A1 | 7/2008 | Duru |
| 2008/0208627 A1 | 8/2008 | Skyggebjerg |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0044397 A1 | 2/2009 | Cohen et al. |
| 2009/0108094 A1 | 4/2009 | Ivri |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0149829 A1 | 6/2009 | Collins, Jr. |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0223513 A1 | 9/2009 | Papania et al. |
| 2009/0272818 A1 | 11/2009 | Valpey, III et al. |
| 2009/0312724 A1 | 12/2009 | Pipkin et al. |
| 2010/0044460 A1 | 2/2010 | Sauzade |
| 2010/0076388 A1 | 3/2010 | Cater |
| 2010/0083956 A1 | 4/2010 | Fukumoto et al. |
| 2010/0111843 A1 | 5/2010 | Boyden et al. |
| 2010/0126502 A1 | 5/2010 | Fink et al. |
| 2010/0144539 A1* | 6/2010 | Bergh ................... G01N 31/10 506/7 |
| 2010/0211408 A1 | 8/2010 | Park et al. |
| 2010/0222752 A1 | 9/2010 | Collins, Jr. et al. |
| 2010/0280466 A1 | 11/2010 | Py et al. |
| 2010/0283601 A1 | 11/2010 | Tai et al. |
| 2011/0092925 A1 | 4/2011 | Voss et al. |
| 2011/0233302 A1 | 9/2011 | Lin et al. |
| 2012/0062840 A1 | 3/2012 | Ballou, Jr. et al. |
| 2012/0070467 A1 | 3/2012 | Ballou, Jr. et al. |
| 2012/0143152 A1* | 6/2012 | Hunter ................. G16H 40/63 604/290 |
| 2012/0318260 A1 | 12/2012 | Hsieh et al. |
| 2013/0085459 A1 | 4/2013 | Voss et al. |
| 2013/0150812 A1 | 6/2013 | Hunter et al. |
| 2013/0172830 A1 | 7/2013 | Hunter et al. |
| 2013/0206857 A1 | 8/2013 | Ivri |
| 2013/0242255 A1 | 9/2013 | Caldarise et al. |
| 2013/0299607 A1 | 11/2013 | Wilkerson et al. |
| 2013/0334335 A1 | 12/2013 | Wilkerson et al. |
| 2014/0151405 A1 | 6/2014 | Kelly |
| 2014/0151457 A1 | 6/2014 | Wilkerson et al. |
| 2014/0171490 A1 | 6/2014 | Gross et al. |
| 2014/0187969 A1 | 7/2014 | Hunter et al. |
| 2014/0249491 A1 | 9/2014 | Ballou, Jr. et al. |
| 2014/0336618 A1 | 11/2014 | Wilkerson et al. |
| 2014/0361095 A1 | 12/2014 | Haran |
| 2015/0034075 A1 | 2/2015 | Gallem et al. |
| 2015/0328151 A1 | 11/2015 | Ballou, Jr. et al. |
| 2015/0340590 A1 | 11/2015 | Ivri |
| 2016/0129088 A1 | 5/2016 | Patton et al. |
| 2016/0250437 A1 | 9/2016 | Fink et al. |
| 2016/0271346 A1 | 9/2016 | Patton et al. |
| 2016/0296367 A1 | 10/2016 | Ivri |
| 2016/0361494 A1* | 12/2016 | Jürg ................... A61M 5/14244 |
| 2017/0136484 A1 | 5/2017 | Wilkerson et al. |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0211959 A1 | 7/2017 | Adler et al. |
| 2017/0344714 A1 | 11/2017 | Ballou, Jr. et al. |
| 2017/0367882 A1 | 12/2017 | Kelly |
| 2018/0021530 A1 | 1/2018 | Fink et al. |
| 2018/0147214 A1 | 5/2018 | Ostrow et al. |
| 2019/0053945 A1 | 2/2019 | Hunter et al. |
| 2019/0192499 A1 | 6/2019 | Puri et al. |
| 2019/0314195 A1 | 10/2019 | Ivri et al. |
| 2020/0019721 A1 | 1/2020 | Shanmugam et al. |
| 2020/0085813 A1 | 3/2020 | Ostrow et al. |
| 2020/0094285 A1 | 3/2020 | Wilkerson et al. |
| 2020/0197218 A1 | 6/2020 | Newell et al. |
| 2020/0197220 A1 | 6/2020 | Ivri |
| 2020/0306239 A1 | 10/2020 | Ostrow et al. |
| 2020/0315842 A1 | 10/2020 | Palanker et al. |
| 2020/0315955 A1 | 10/2020 | Soppimath et al. |
| 2020/0337896 A1 | 10/2020 | Ianchulev et al. |
| 2020/0338060 A1 | 10/2020 | Ostrow et al. |
| 2020/0345542 A1 | 11/2020 | Ostrow et al. |
| 2020/0352928 A1 | 11/2020 | Puri et al. |
| 2020/0397775 A1 | 12/2020 | Mohammed et al. |
| 2020/0397776 A1 | 12/2020 | Mohammed et al. |
| 2020/0405705 A1 | 12/2020 | Mohammed et al. |
| 2021/0121395 A1 | 4/2021 | Soppimath et al. |

(56) References Cited

U.S. PATENT DOCUMENTS

| | | | |
|---|---|---|---|
| 2021/0128350 A1 | 5/2021 | Ivri et al. | |
| 2021/0128546 A1 | 5/2021 | Soppimath et al. | |
| 2021/0177650 A1 | 6/2021 | Clauson et al. | |
| 2021/0295989 A1 | 9/2021 | Ballou, Jr. et al. | |

FOREIGN PATENT DOCUMENTS

| | | |
|---|---|---|
| DE | 196 16 300 A1 | 10/1997 |
| DE | 199 34 582 C2 | 9/2003 |
| DE | 102 36 669 A1 | 2/2004 |
| EP | 0 011 269 B1 | 4/1983 |
| EP | 0 150 571 A1 | 8/1985 |
| EP | 0 224 352 B1 | 8/1990 |
| EP | 0 389 665 A1 | 10/1990 |
| EP | 0 590 165 B1 | 2/1997 |
| EP | 0 933 138 B1 | 3/2004 |
| EP | 1 219 314 B1 | 3/2004 |
| FR | 1 271 341 A | 9/1961 |
| FR | 2 934 128 A1 | 1/2010 |
| GB | 558866 A | 1/1944 |
| GB | 1 569 707 A | 6/1980 |
| GB | 2 272 389 A | 5/1994 |
| JP | S62-142110 A | 6/1987 |
| JP | H8-52193 A | 2/1996 |
| JP | 2000-043243 A | 2/2000 |
| JP | 2002-191560 A | 7/2002 |
| JP | 2003-501157 A | 1/2003 |
| JP | 3104861 U | 10/2004 |
| JP | 2005-515841 A | 6/2005 |
| JP | 2005-288009 A | 10/2005 |
| JP | 2008-515625 A | 5/2008 |
| JP | 2009-072313 A | 4/2009 |
| JP | 2012-508129 A | 4/2012 |
| KR | 10-2015-0020542 A | 2/2015 |
| TW | I293898 B | 3/2008 |
| WO | WO-85/00761 A1 | 2/1985 |
| WO | WO-91/12687 A1 | 8/1991 |
| WO | WO-91/14468 A1 | 10/1991 |
| WO | WO-94/13305 A1 | 6/1994 |
| WO | WO-94/23788 A1 | 10/1994 |
| WO | WO-95/15822 A1 | 6/1995 |
| WO | WO-95/26236 A1 | 10/1995 |
| WO | WO-96/00050 A1 | 1/1996 |
| WO | WO-96/06581 A1 | 3/1996 |
| WO | WO-97/05960 A1 | 2/1997 |
| WO | WO-97/12687 A1 | 4/1997 |
| WO | WO-97/23177 A1 | 7/1997 |
| WO | WO-98/08479 A1 | 3/1998 |
| WO | WO-98/19383 A1 | 5/1998 |
| WO | WO-99/17888 A1 | 4/1999 |
| WO | WO-00/18455 A1 | 4/2000 |
| WO | WO-00/66277 A1 | 11/2000 |
| WO | WO-01/03645 A2 | 1/2001 |
| WO | WO-01/19437 A1 | 3/2001 |
| WO | WO-01/58236 A2 | 8/2001 |
| WO | WO-01/68169 A1 | 9/2001 |
| WO | WO-01/85245 A1 | 11/2001 |
| WO | WO-02/28545 A1 | 4/2002 |
| WO | WO-02/055131 A2 | 7/2002 |
| WO | WO-02/062488 A1 | 8/2002 |
| WO | WO-02/072169 A2 | 9/2002 |
| WO | WO-03/002045 A1 | 1/2003 |
| WO | WO-03/002265 A1 | 1/2003 |
| WO | WO-03/026556 A2 | 4/2003 |
| WO | WO-03/097139 A1 | 11/2003 |
| WO | WO-2004/028420 A1 | 4/2004 |
| WO | WO-2004/050065 A1 | 6/2004 |
| WO | WO-2004/080367 A2 | 9/2004 |
| WO | WO-2004/084116 A1 | 9/2004 |
| WO | WO-2004/103478 A1 | 12/2004 |
| WO | WO-2004/105864 A1 | 12/2004 |
| WO | WO-2005/102058 A2 | 11/2005 |
| WO | WO-2006/006963 A2 | 1/2006 |
| WO | WO-2006/050838 A2 | 5/2006 |
| WO | WO-2006/082588 A2 | 8/2006 |
| WO | WO-2007/056233 A1 | 5/2007 |
| WO | WO-2007/115087 A1 | 10/2007 |
| WO | WO-2008/015394 A1 | 2/2008 |
| WO | WO-2008/087250 A1 | 7/2008 |
| WO | WO-2008/125128 A1 | 10/2008 |
| WO | WO-2009/055733 A1 | 4/2009 |
| WO | WO-2009/148345 A2 | 12/2009 |
| WO | WO-2011/117212 A1 | 9/2011 |
| WO | WO-2012/009696 A2 | 1/2012 |
| WO | WO-2012/009702 A1 | 1/2012 |
| WO | WO-2012/009706 A1 | 1/2012 |
| WO | WO-2013/158967 A2 | 10/2013 |
| WO | WO-2015/123656 A1 | 8/2015 |
| WO | WO-2016/115050 A1 | 7/2016 |
| WO | WO-2016/164830 A1 | 10/2016 |
| WO | WO-2018/136618 A2 | 7/2018 |
| WO | WO-2019/104191 A1 | 5/2019 |
| WO | WO-2019/113483 A1 | 6/2019 |
| WO | WO-2020/010116 A1 | 1/2020 |
| WO | WO-2020/180793 A1 | 9/2020 |

OTHER PUBLICATIONS

Becker, E.W. et al. (1986). "Fabrication of microstructures with high aspect ratios and great structural heights by synchrotron radiation lithography, galvanoforming, and plastic moulding (LIGA process)." *Microelectronic Engineering*, vol. 4, Issue 1, 35-56.

Brown et al. (1965). "The Preservation of Ophthalmic Preparations." Journal of the Society of Cosmetic Chemists, vol. 16:369-393.

Cheng, C .H. et al. (2005). "Multilevel electroforming for the components of a microdroplet ejector by UV LIGA technology." *Journal of Micromechanics and Microengineering*. 15. 843-848. doi: 10.1088/0960-1317/15/4/023.

Conover (Ed.), "View into the Future of Ophthalmology Treatments," Healthcare Observer, 1(8):2-37, (2009).

Dhand, "Nebulizers That Use a Vibrating Mesh or Plate with Multiple Apertures to Generate Aerosol," Respir Care, 47(12):1406-1418, (2002).

Donnelly et al., "Using ultrasonic atomization to produce an aerosol of micron-scale particles," Review of Scientific Instruments, 76:113301-1-113301-10, (2005).

Durnan et al., "Gold-Chlorine and Gold-Bromine Equilibria in Fused Salts," The Journal of Physical Chemistry, 68(4):847-850, (1964).

Galambos et al., "Drop ejection utilizing sideways actuation of a MEMS piston," Sensors and Actuators A, 141:182-191, (2008).

Hinds. "Aerosol Technology: Properies, Behavior, and Measurement of Airborne Particles," pp. 42-71, 111-119, & 294-301, (1999).

Instruction Manual for Omron. RTM. Model NE-U03V MicroAir. RTM. Nebulizer, 20 pages, (No date).

International Search Report dated Dec. 12, 2011, in International Application No. PCT/US2011/044291. 5 pages.

International Search Report dated Dec. 13, 2011, in International Application No. PCT/US2011/044286. 6 pages.

Ming, Jr., L. et al. (2010, published Dec. 14, 2009), "Influence of liquid hydrophobicity and nozzle passage curvature on microfluidic dynamics in a drop ejection process," *Journal of Micromechanics and Microengineering*, vol. 20:015033, 14 pp, XP020168894.

Miyajima, H. et al. (Dec. 1995), "High-Aspect-Ratio Photolithography for MEMS Applications." *Journal of Microelectromechanical Systems*, vol. 4, No. 4, pp. 220-229, doi: 10.1109/84.475549.

Ostendorf, A. et al. (Apr. 1, 2002). "Development of an industrial femtosecond laser micromachining system," *Proc. SPIE 4633, Commercial and Biomedical Applications of Ultrafast and Free-Electron Lasers*, vol. 4633, pp. 128-135, https://doi.org/10.1117/12.461372.

Product Description for Xalatan. RTM: latanoprost opthalmic solution, Pfizer Manufacturing, Belgium, NV, 8 pages, (2009).

Quigley, "Improving Eye Drop Treatment for Glaucoma through Better Adherence," Optometry and Vision Science, 85(6):374-375, (2008).

(56) References Cited

OTHER PUBLICATIONS

Ranade et al., "Chapter seven: Intranasal and ocular drug delivery," Drug Delivery Systems: Second Edition, CLC Press, 39 pages, (2004).

Rosen et al., "Printing High Viscosity Fluids Using Ultrasonic Droplet Generation," The George W. Woodruff School of Mechanical Engineering, Georgia Institute of Technology, pp. 239-253, (2008).

Santvliet, L.V., et al. (2004). "Determinants of eye drop size." Survey of Ophthalmology, 49(2), 197-211. https://doi.org/10.1016/j.survophthal.2003.12.009.

Shidhaye et al., "Novel drug delivery devices," Pharma Times, 38(7):24-27, (2006).

Tamilvanan et al., "The potential of lipid emulsion for ocular delivery of lipophilic drugs," European Journal of Pharmaceutics and Biopharmaceutics, 58:357-368, (2004).

Xia et al., "A potential application of a piezoelectric atomiser for opthalmic drug delivery," BOB, 4(1):9-17, (2007).

Yee et al., "Trends in Glaucoma Treatment," EyeWorld Educational Symposium, San Francisco, 8 pages, (2006).

Yuan et al., "MEMS-based piezoelectric array microjet," Microelectronic Engineering, 66:767-772, (2003).

U.S. Appl. No. 15/197,033, filed Jun. 29, 2016, US 2017-0136484.
U.S. Appl. No. 16/434,428, filed Jun. 7, 2019, US 2020-0094285.
U.S. Appl. No. 16/621,564, filed Dec. 11, 2019, US 2020-0197218.
U.S. Appl. No. 17/091,607, filed Nov. 6, 2020, US 2021-0295989.
PCT/US2020/064648, Dec. 11, 2020, WO 2021/119513 A1.

Edelhauser, H.F. et al. (1979). "The Effect of Phenylephrine on the Cornea." Arch Ophthalmol.; 97(5):937-947.

Ratanapakorn, T. et al. (2006). "Single dose of 1% tropicamide and 10% phenylephrine for pupil dilation." Journal of the Medical Association of Thailand, 89(11), 1934-1939.

U.S. Appl. No. 16/962,608, filed Jul. 16, 2020, US 2020-0337896.
U.S. Appl. No. 17/119,905, filed Dec. 11, 2020, US 2021-0177650.
U.S. Appl. No. 17/239,832, filed Apr. 26, 2021, US 2021-0398651.
U.S. Appl. No. 17/319,401, filed May 13, 2021, US 2021-0407663.
U.S. Appl. No. 17/397,874, filed Aug. 9, 2021, US 2022-0062035.
U.S. Appl. No. 17/434,711, filed Aug. 27, 2021, US 2022-0125631.
U.S. Appl. No. 17/704,395, filed Mar. 25, 2022, US 2022-0355329.
U.S. Appl. No. 17/849,425, filed Jun. 24, 2022, US 2022-0395221.
U.S. Appl. No. 17/994,693, filed Nov. 28, 2022, US 2023-0173118.

\* cited by examiner

METHODS AND DEVICES FOR HANDLING A FLUID AND DELIVERING THE FLUID TO THE EYE

PRIORITY

This patent application is a 371 of PCT Patent Application No. PCT/US2018/036908, filed Jun. 11, 2018, and entitled "METHODS AND DEVICES FOR HANDLING A FLUID AND DELIVERING THE FLUID TO THE EYE," which claims the benefit under 35 U.S.C. § 119(e) of U.S. Provisional Patent Application No. 62/517,914, filed Jun. 10, 2017, and entitled "METHODS AND DEVICES FOR HANDLING A FLUID AND DELIVERING THE FLUID TO THE EYE, each of which is incorporated herein by reference in its entirety.

FIELD OF THE INVENTION

The invention is directed to methods and devices for handling a fluid and for delivering the fluid to the eye.

BACKGROUND OF THE INVENTION

Fluid delivery to the eye presents a number of challenges. The fluid should be provided with a controlled droplet size and delivered at a controlled velocity for comfort while delivered at high enough velocity to deliver the entire dose. Another challenge with fluid delivery to the eye is the need for rapid delivery so that an eye blink does not interfere with delivery.

Fluid delivery devices for the eye have used a piezoelectric element to vibrate an element, such as a plate, with holes through which the fluid is ejected. A problem with many of these devices is that they are typically "wet" systems in which the fluid is exposed through the holes in the plate when stored which may lead to undesirable evaporation and contamination between uses.

SUMMARY OF THE INVENTION

The present invention is directed to methods and devices for handling a fluid and delivering the fluid to the eye. In one aspect, the fluid to be delivered to the eye is contained in an enclosure which holds the fluid to be dispensed in a chamber defined by the enclosure. The enclosure holds the dose of fluid in proximity to the openings so that the fluid may be ejected in a short amount of time and with little residual volume left.

The enclosure has a lip positioned adjacent a vibrating element having openings through which the fluid is ejected. The lip may be unattached to the vibrating element but still in contact with the vibrating element or may be spaced apart a short distance so that surface tension holds the fluid in the chamber. The vibrating element may have a relatively small maximum amplitude when vibrated which is less than an average separation distance between the lip and the vibrating element or less than a minimum separation distance between the lip and the vibrating element.

The enclosure may also be shaped to cooperate with the vibrating element to avoid capillary feed near the openings in the vibrating element. To this end, the enclosure may be spaced apart from the vibrating element so that at least 75%, at least 95%, or all of the openings are spaced at least 0.014 from the nearest part of the enclosure. Capillary feed may be incorporated in other aspects of the invention without departing from those aspects of the invention. The enclosure is also shaped so that all of the fluid can reach the openings in a short period of time. The enclosure has an internal surface in contact with the fluid shaped so that at least 75%, at least 95%, or even all, of the internal surface is no more than 0.060 inch, or no more than 0.040 inch, from a nearest of the plurality of openings. Stated another way, the enclosure has an internal surface shaped so that the chamber is formed with at least 75%, at least 95%, or all, of the internal surface has direct line of sight to at least one of the openings. The inner surface of the enclosure may be hydrophobic over at least 70% of the inner surface in contact with fluid.

The lip may be biased against the vibrating element with a modest force to prevent the fluid from escaping while not overly dampening vibrations. The lip may exert a force of no more than 3 gram-f on the vibrating element measured in the direction of a central axis of the vibrating element. The lip may also apply a spring load to the vibrating element so that minor displacements due to temperature, pressure or shock from an impact (dropped) can be accommodated. The spring load may also help to address manufacturing tolerances which affect the load applied by the lip to the vibrating element. The lip may exert a spring load on the vibrating element with an average spring constant of no more than 60 gram-f/mm for displacements up to 0.050 mm. The enclosure itself may be resilient with a wall of the enclosure having a tapered portion with a relatively thin wall to provide flexibility. The tapered portion of the wall and has a ratio of radial displacement to longitudinal displacement of at least 1 to 3, at least 1 to 2 and may be at least 1 to 1. Stated another way, the tapered portion also extends radially with respect to the open end of the enclosure for at least half of an effective radius of the open end of the enclosure. The lip and/or the vibrating element may have a PTFE coating adjacent to the other to reduce friction therebetween. The coating(s) may extending around at least 270 degrees when viewed along the central axis.

The enclosure may allow air into to replace ejected fluid through the openings and/or between the lip and the vibrating element and may include no dedicated vent opening. The maximum amplitude may be somewhat small which permits air to enter the chamber while still preventing fluid from escaping from the chamber. The enclosure to vibrating element interface defines an enclosed border (which may be defined by either the vibrating element or the enclosure) which is somewhat larger than the extent of the openings with an excess area which extends radially outwardly at least 0.3 times the effective radius of the enclosed feed area.

The enclosure may include a wall opening through the wall which exposes the chamber through the wall. The wall opening. The wall opening extends through the wall to expose the chamber through the wall without permitting fluid to escape while permitting air to enter when fluid is ejected. The wall opening has a longitudinal dimension measured from the lip in the direction of the central axis and a radial dimension measured in a radial direction relative to the central axis. The enclosure also has an internal wall with a side facing the openings in the vibrating element. The longitudinal dimension of the wall opening is at least 80% of a separation distance between the vibrating element and the side of the enclosure facing the openings. The radial dimension of the wall opening may be no more than 10%, or no more than 5%, of a equivalent circumference of the lip.

The wall opening tapers as it extends proximally away from the lip. The wall opening extends from the lip proximally and a circumferential dimension of the wall opening tapers down as the wall opening extends proximally from the lip. The wall opening tapers so that a tapered shape is oriented in the direction of the fluid inlet to the chamber when viewed along the central axis. The wall opening may also extend through the frustoconical portion of the wall and may extend proximally from the lip for at least 80% of the length of the frustoconical portion.

The fluid may be delivered rapidly and at relatively high velocity and pressure to encourage all of the fluid to gather in the chamber. The total downstream volume of the fluid path from a pump or valve which isolates the chamber may be sized somewhat larger than the volume to permit the fluid to move within the enclosure somewhat and coalesce into a single droplet due to surface tension. The volume of the fluid may be 40%-70% of the total downstream volume.

The enclosure may also split the fluid flow into at least two (and may be three, four or more) inlets to the chamber. Each of the inlets directs the fluid at a sidewall before being directed at the plurality of openings. The enclosure has a main inlet which directs the flow in a direction within 30 degrees of the central axis while the inlets to the chamber are oriented 60-90 degrees from the central axis and directed at the sidewall. The enclosure may be an integrally formed structure which defines the chamber.

The pump may have a first part and a second part which reciprocate between a stored position, to a forward stroke position and back to the stored position in a single cycle. A cavity is formed between the two parts in which the fluid is drawn and subsequently expelled into the chamber. An air make-up chamber may also be coupled to the pump to force air into a fluid container during each cycle to actively vent the fluid container.

The present invention may be practiced as a device or method. As to the device it is understood that a therapeutic delivery device may be separated into reusable and disposable portions in innumerable different combinations. As such, the present invention provides inventive concepts that may be logically grouped together in various ways which define a subset of the device which may be a disposable or reusable portion. For example, the fluid container may be replaced with the enclosure or may be independent and, therefore, may be claimed in either manner. The enclosure may form part of a reusable device together with the vibrating element or may be part of a disposable (with or without the fluid container) without departing from the scope of the invention. The claimed invention lies in the methodology and structure rather than in specific delineation or the disposable and reusable parts. Thus, it is understood that the disposable parts may be defined in virtually any suitable manner and the claims may define any such limited aspect or combination. As further examples, the claims may define the pump and the fluid container, the enclosure and the vibrating element, or even a single structure such as the enclosure by itself. Each of these could be part of reusable device, a single-use device, or as a disposable and may be claimed as such.

These and other features will become apparent from the following description of the preferred embodiments, claims and drawings.

DESCRIPTION OF THE PREFERRED EMBODIMENTS

Figure 1:
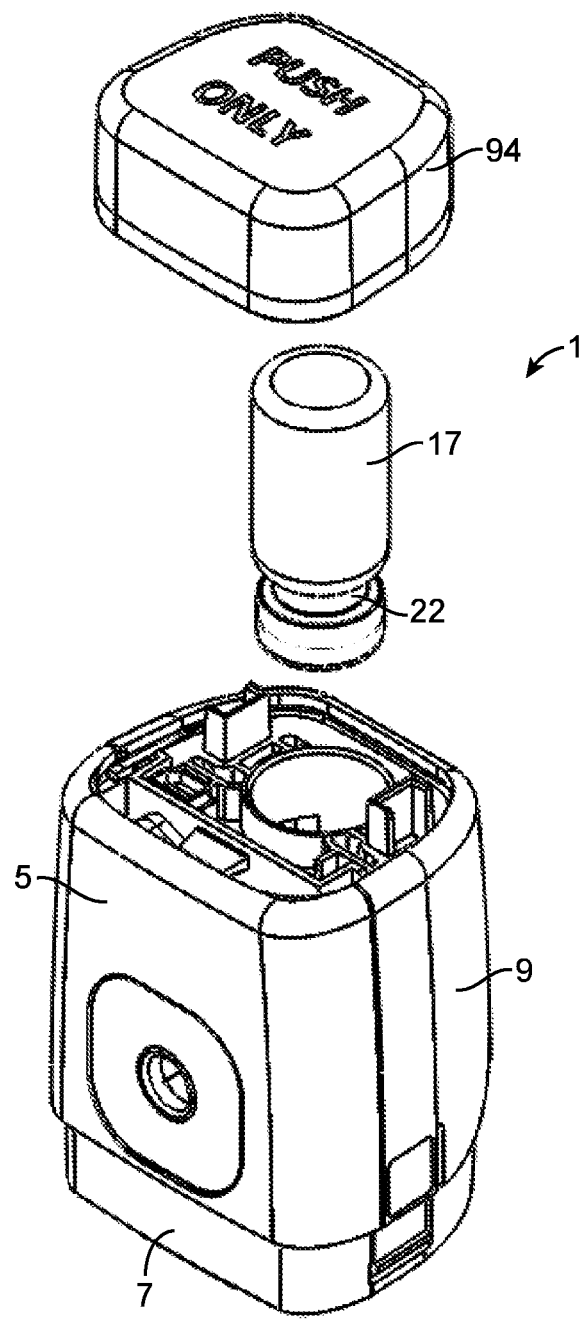
FIG. 1 shows a device for handling a fluid and delivering the fluid to the eye with a cap removed for introducing a fluid container.
Figure 2:
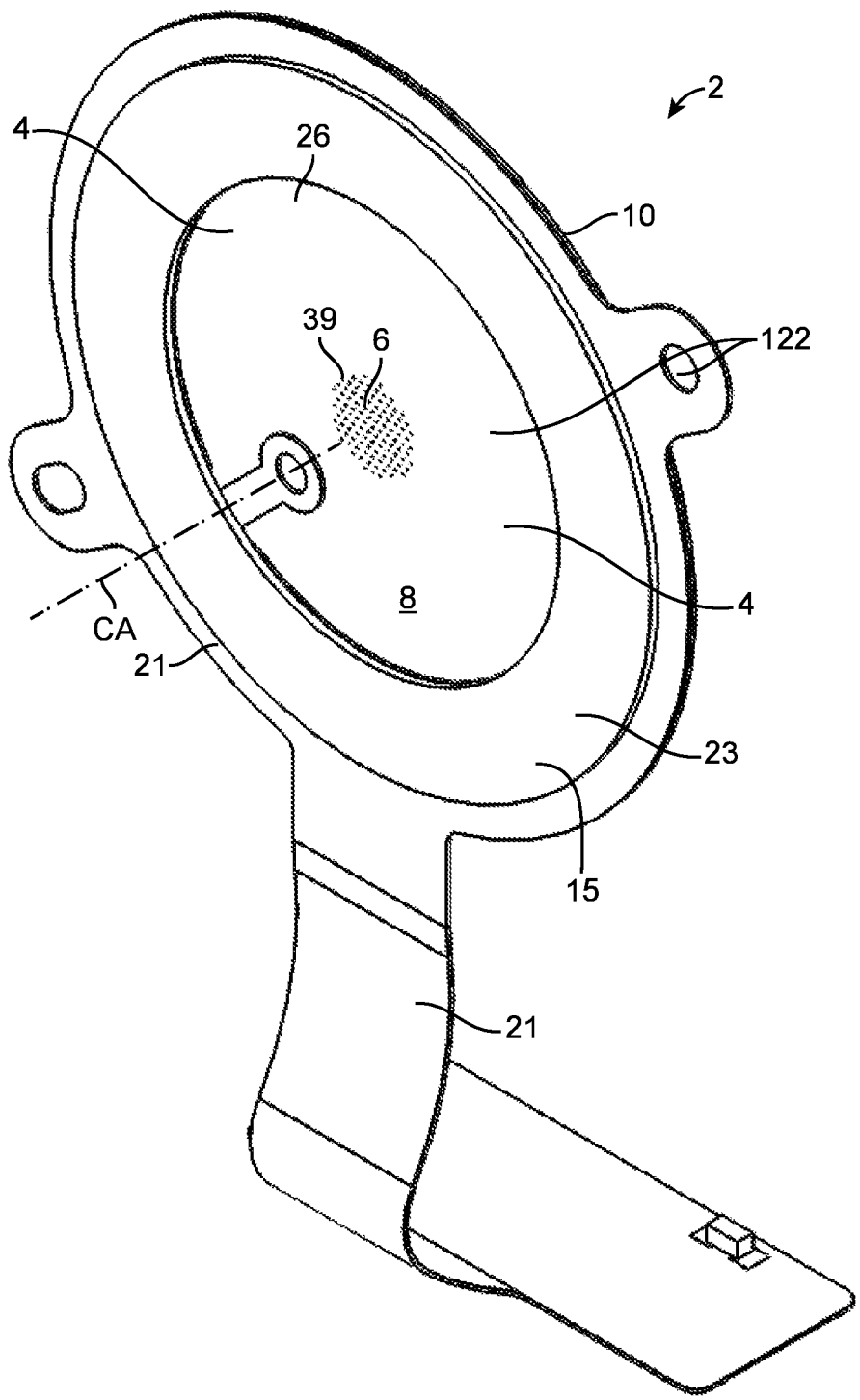
FIG. 2 shows a vibrating element with openings through which the fluid is ejected.
Figure 7:
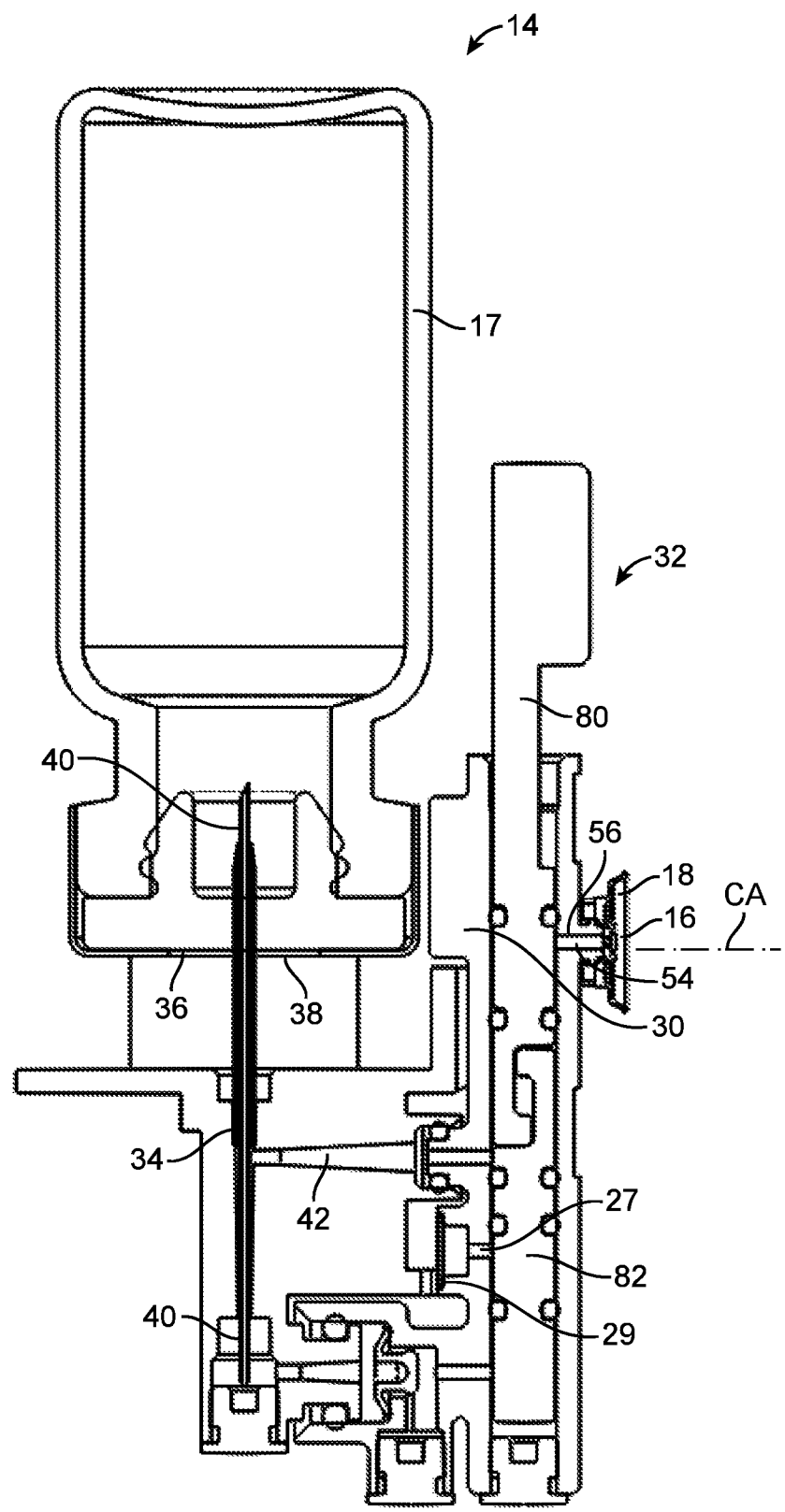
FIG. 7 shows the fluid delivery path from the fluid container to an enclosure.
Figure 10:
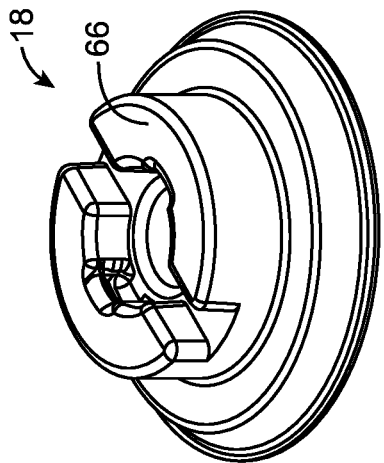
FIG. 10 shows a perspective view of the enclosure.
Figure 9:
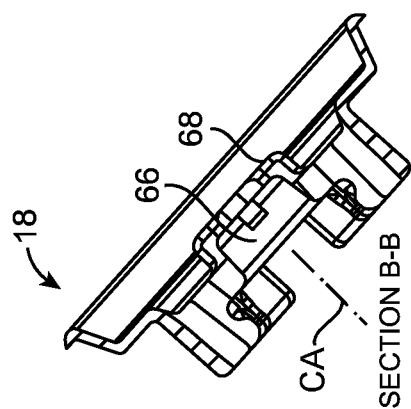
FIG. 9 shows another cross-section of the enclosure.
Figure 8:
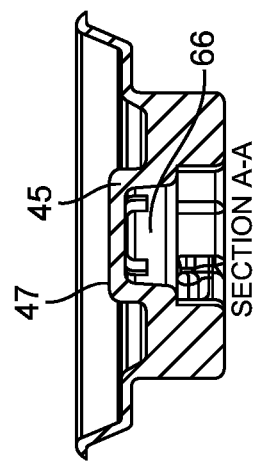
FIG. 8 shows a cross-section of the enclosure.
Figure 11:
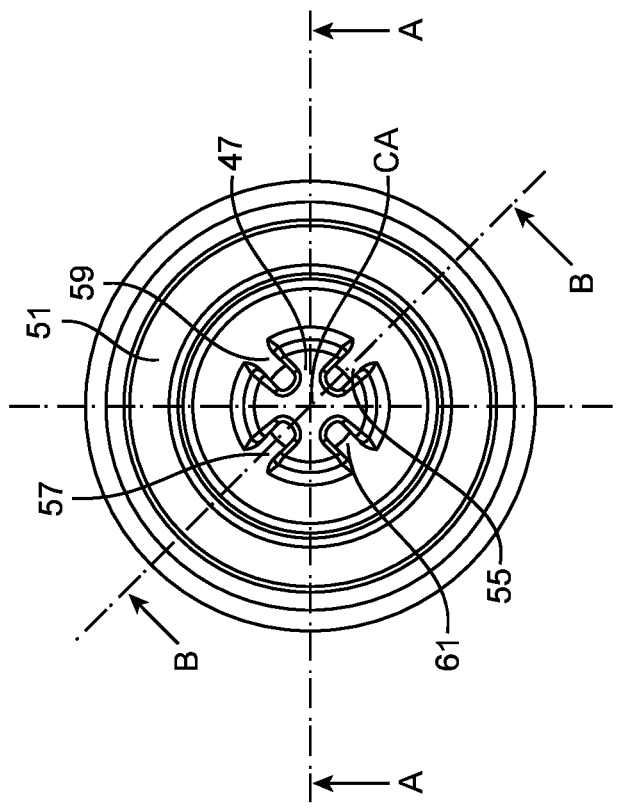
FIG. 11 shows a bottom view of the enclosure including the flow splitting chamber.
Figure 12:
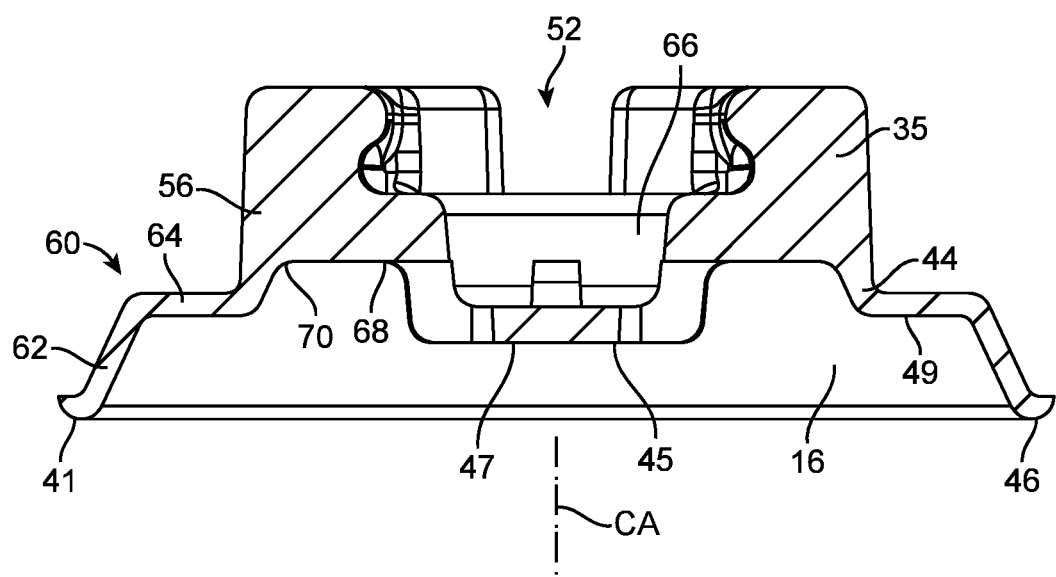
FIG. 12 shows an enlarged cross-sectional view of the enclosure.

The present invention is directed to methods and devices for handling a fluid and delivering the fluid to the eye. Referring to FIGS. 1, 2 and 7, a device 1 is shown which includes a fluid ejector 2 (FIG. 2) and a fluid handler 14 (FIG. 7). The fluid ejector 2 includes a vibrating element 4 having a plurality of openings 6 which is vibrated with a piezoelectric element 15 coupled to the vibrating element 4. The term fluid as used herein refers to any flowable substance and does not refer only to the liquid state of a material.

Figure 5:
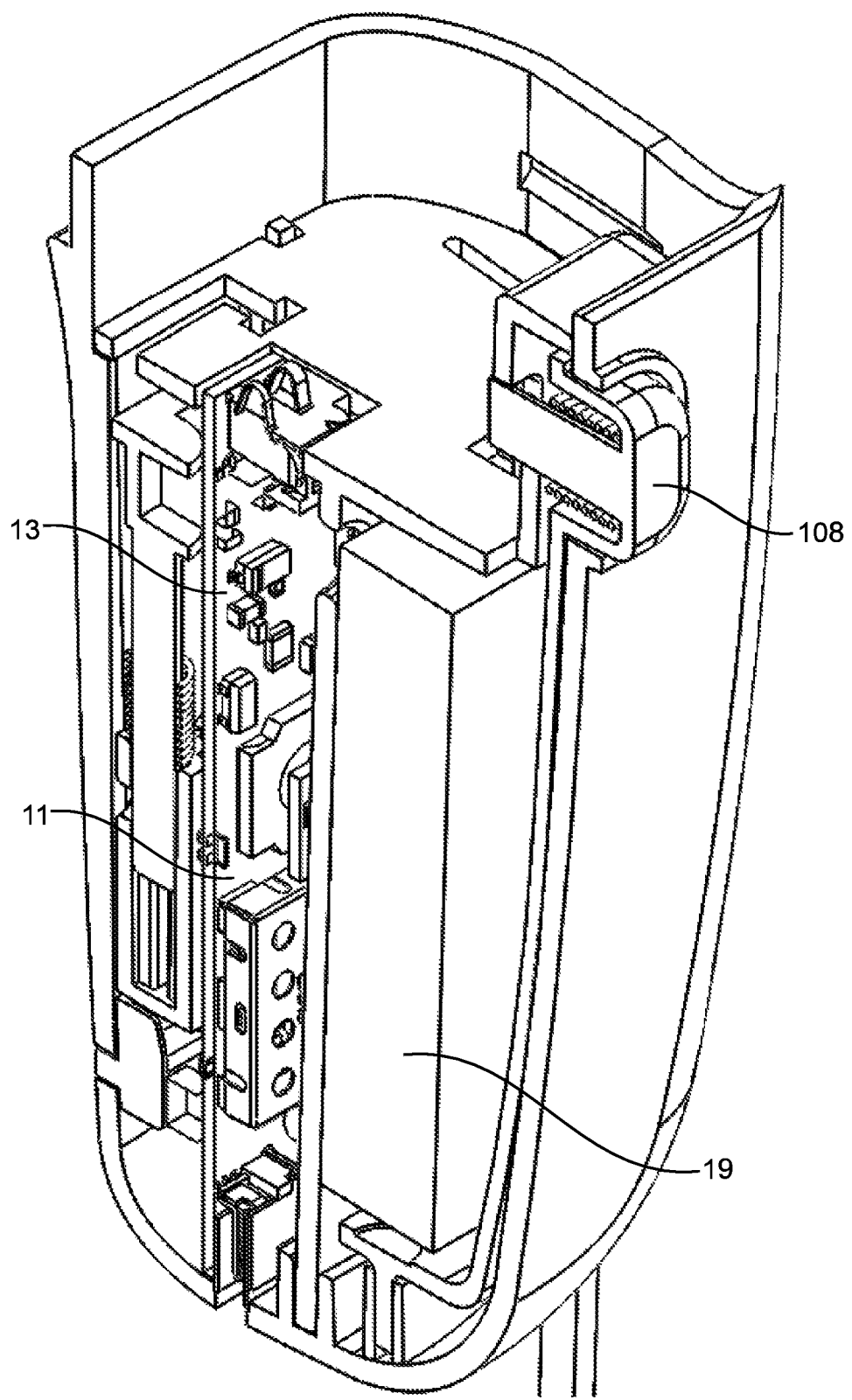
FIG. 5 shows a cross-section of a second housing part which houses the control system and battery.
Figure 6:
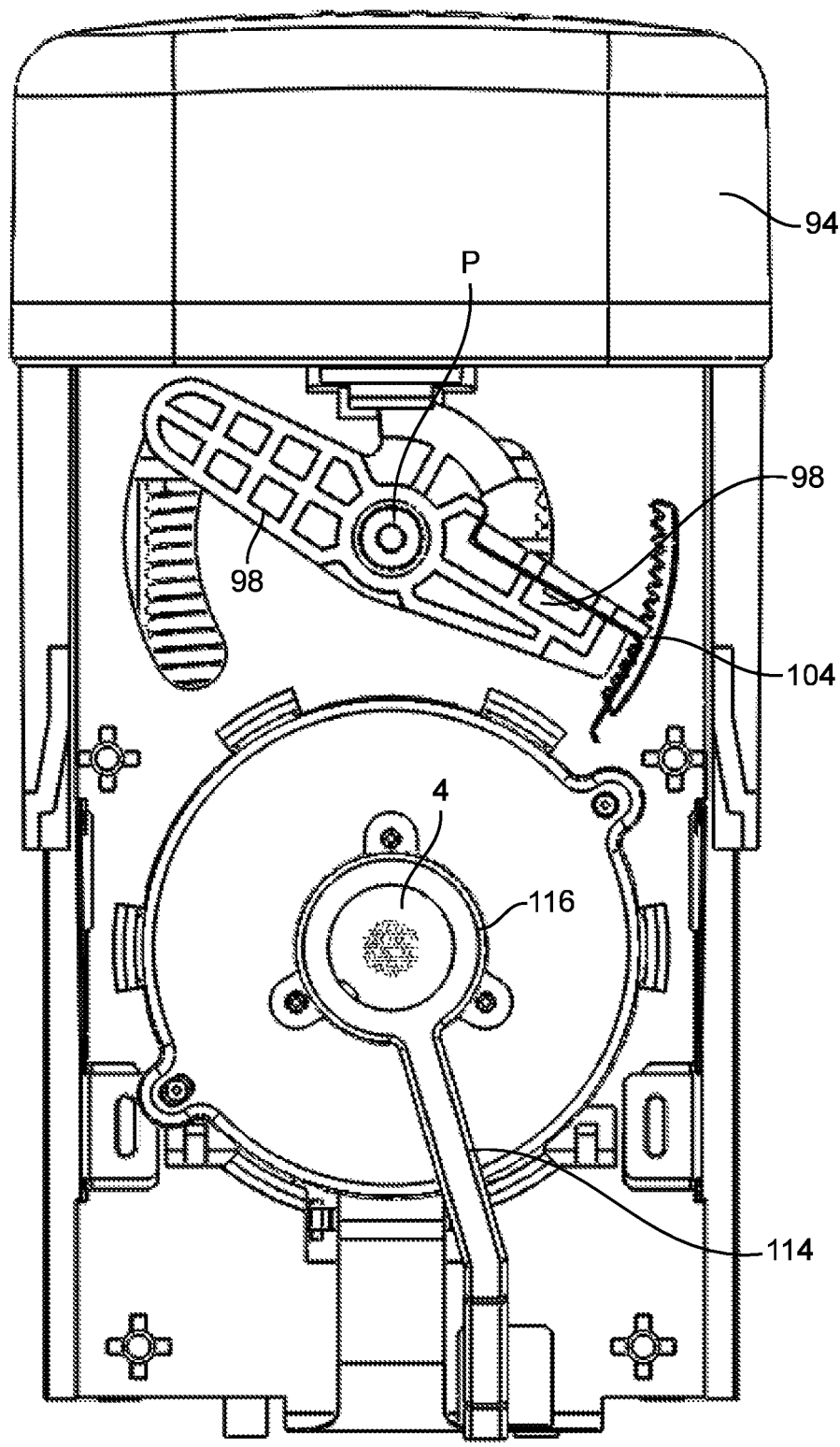
FIG. 6 shows a front view of the device with the outer cover removed.

The device 1 has a housing 5 which may include a first housing part 7 and a second housing part 9 which lock together with any suitable engagement such as a twist or snap-fit. Referring to FIG. 5, a control system 11 which includes a printed circuit board 13 is mounted to the first housing part 7. The control system 11 is coupled to and controls the piezoelectric element 15 as is known in the art. A battery 19 powers the control system 13 and the driving electronics for the piezoelectric element 15 as is known in the art. The fluid handling system 14 is coupled to the second housing part 9. The control system 11 may be reusable while the fluid handler 14 may be disposable. Furthermore, the fluid may be held in a fluid container 17 which may be locked to the first housing 7 to prevent removal so that the fluid handler 14 is disposable after (with) the first fluid container 17. Of course, the fluid handling system 14 may also be used with more than one container 17 or the container 17 may have a reservoir that is filled without departing from numerous aspects of the invention. Furthermore, the entire system 1 may be disposable or reusable or separated into disposable and reusable portions in any manner without departing from most aspects of the present invention.

The piezoelectric element 15 may be an annular disc 23 coupled to either a delivery side 8 or a fluid side 10 of the vibrating element 4 with the openings 6 positioned in an open central region 26 of the annular disc 23. The piezoelectric element 15 may be made of any suitable material (such as Lead zirconate titanate; an intermetallic inorganic compound with the chemical formula $Pb[Zr_xTi_{1-x}]O_3$). The piezoelectric element 15 may be bonded, adhered, molded or otherwise coupled to the vibrating element in any suitable manner as is known in the art. A flexible circuit 21 is in electrical communication with the piezoelectric element 15 to control the piezoelectric element 15. The flexible circuit 21 is coupled to the control system 1 (see FIG. 5) which controls the piezoelectric element 15 to induce vibrations in the piezoelectric element to vibrate the element 4 and eject fluid from the openings 6. The vibrating element 4 is vibrated at a frequency of 100 to 160 khz which may be a resonant frequency. The resonant frequency may be predetermined, measured, determined or tuned as is known in the art. The driving frequency of the piezoelectric element 15 is described further below. Of course, the frequency of operation may be at a frequency other than a resonant frequency.

The fluid side 10 of the vibrating element 4 at the openings 6 is in contact with the fluid to be delivered and ejects the fluid to the delivery side 8. Fluid is ejected through the openings 6 toward the eye when the vibrating element 4 is vibrated. The openings 6 may taper from the fluid side 10 to the delivery side 8. For example, the opening 6 at the fluid side may have a diameter of 160-240 microns (and may be 200 microns) while the diameter at the delivery side may be 20-60 microns (and may be 40 microns). A column of consistent diameter (20-60 microns) extends to the delivery side 8 and has a length of 10-40 microns and may be about 25 microns in length. The openings 6 may have a curved wall between the fluid and delivery sides with a radius of curvature of 100 microns. The openings 6 at the fluid side 10 and the delivery side 8 may have a circular cross-sectional shape. As used herein, the cross-sectional area (or other dimension) may be defined by an effective diameter (or effective radius) for a circle having the same area.

The vibrating element 4 may have a thickness of 100 to 180 microns, or 120-160 microns, and may be about 140 microns, and may be made of any suitable material such as PEEK or Polyimide, with additional layers consisting of copper, polyimide, nickel, and/or gold. The vibrating element 4 may have a thickness of 125 microns and the coating/plating having a total thickness of about 15 microns so that the vibrating element 4 has thickness of about 140 microns. Of course, numerous other configurations may be practiced within the scope of the invention with respect to the materials and manufacture of the vibrating element 4 and piezoelectric element 15 and dimensions of the openings 6.

Fluid may be ejected so that an average ejection velocity is 2.5 m/s to 15 m/s, as it leaves the opening 6 at the delivery side 8 and may be about 5-6 m/s. The vibrating element 4 defines a central axis CA which is a central orientation of the plurality of openings 6 defined by a geometric center of the ejection orientation of the plurality of openings 6. For a circular pattern of openings 6 of even density distribution with a flat vibrating element 4 the central axis CA extends perpendicular to plane of vibrating element 4 at the center of the circular pattern of openings 6. Stated another way, the central axis CA is perpendicular to a plane defined by the vibrating element 4 and is aligned with the geometric center of the ejection direction that the openings 6 are aligned or with a geometric center of a spray pattern created by the plurality of openings 6. The central axis CA may be defined by an average or geometric center without departing from scope of the invention when, for example, the openings 6 are clustered or an irregular or asymmetrical shape or varying density of openings 6 (number of openings)/mm2 as used herein.

Figure 3:
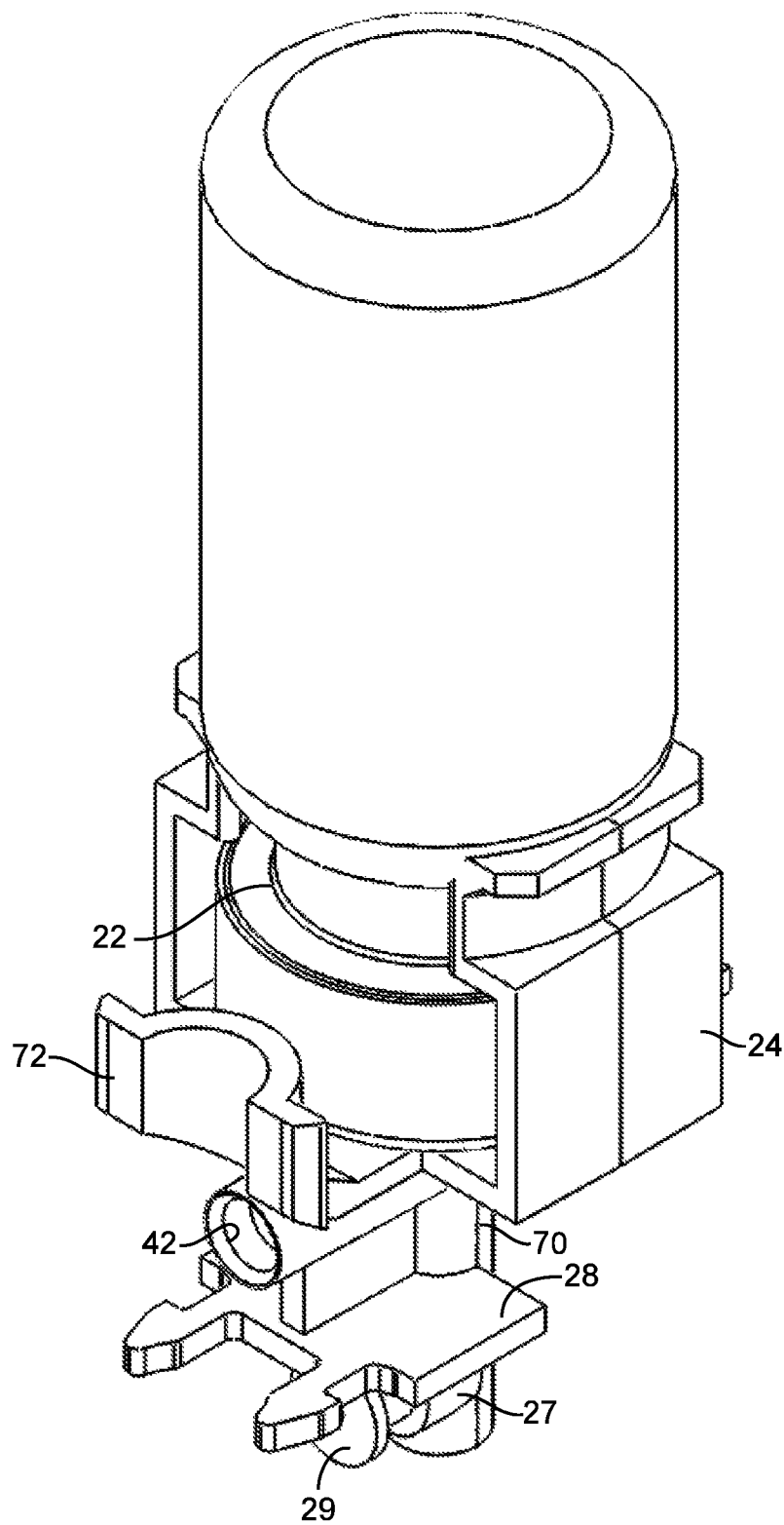
FIG. 3 shows the locking mechanism for the fluid container.

Referring to FIGS. 1, 3 and 7, multiple doses of the fluid are stored in the fluid container 17 which is locked to the housing 5 (specifically the second part 9) when a recess 22 engages locking tabs 24 on a container lock 26. A snap-fit connector 28 (FIG. 3) locks to a manifold 30 (FIG. 7) of a pump 32 described below. When the container 17 is pushed downward and locked to the housing 5, a fluid delivery needle 34 passes through a pierceable element 36 such as a septum 38 in the container 17. A vent needle 40, which may be independent or concentrically arranged with the fluid delivery needle 34, also passes through the pierceable element 36. Fluid is drawn from the container 17 through a fluid conduit 42 with the pump 32 as explained further below. Air is drawn into an air intake lumen 27 (covered by a filter 29) which is used to vent the container 17 as explained below.

Figure 22:
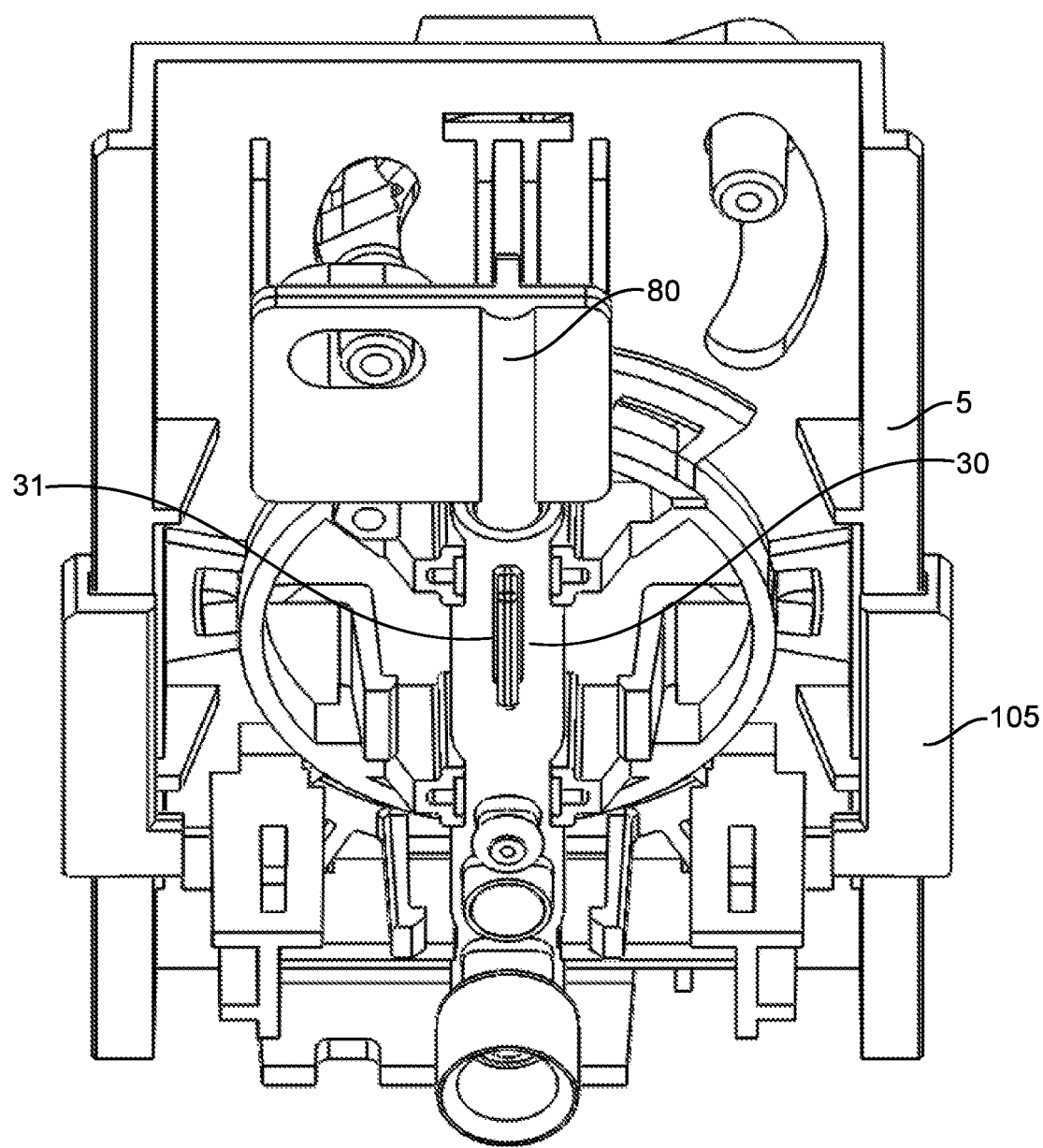
FIG. 22 shows a perspective view of the device with the pump return springs removed.

Referring to FIGS. 7-12, individual doses of the fluid are delivered to a chamber 16 formed by an enclosure 18 and the vibrating element 4. The chamber 16 may be substantially dry after delivery of the fluid and dry when stored which may provide advantages over "wet" systems which may suffer from undesirable contamination or evaporation. The enclosure 18 has a wall 44 with a lip 46 positioned adjacent the fluid side of the vibrating element 4. The lip 46 extends around the plurality of openings 6. The enclosure 18 and the vibrating element 4 together define the chamber 16 or the chamber 16 may be defined by the enclosure 18 bounded by an open end 33 of the enclosure 18 while the. open end 33 is bounded and defined by the lip 46. The wall 44 extends from the open end 33 to a hub 35 which has a main inlet 52. The main inlet 52 is coupled to a lumen 54 formed in a tube 56 through which fluid is delivered by the pump 32. The enclosure 18 may be formed together with the tube 56 or as separate parts as shown. The tube 56 may be formed with the manifold 30 which may be defined as part of the pump 32 so that the pump 32 delivers the fluid directly to the enclosure 18. The manifold 30 has a mounting rib 31 (FIG. 22) which engages the housing. The tube 56 may also be defined separate from the pump 32 as used herein, for example, the tube 56 may be part of the enclosure 18 (either as a disposable or a resuable part).

The lip 46 of the enclosure 18 is positioned adjacent to the fluid side 10 of the vibrating element 4 to prevent the fluid from escaping or leaking between the lip 46 and the vibrating element 4. The lip 46 and the vibrating element 4 are adjacent one another along a closed loop which encircles the openings 6 and has a diameter of 0.190-0.240 inch and may be 0.210 inch. The enclosure 18 also defines a central axis CA which is a geometric center of an area bounded by the lip 46 at the open end of the enclosure 18 and oriented perpendicular to the area bounded by the lip 46. As used herein, the term central axis CA may mean any one of the definitions herein applicable and may be interchanged when applicable and such substitutions are expressly incorporated wherever the term central axis CA is used such as when the two are co-linear. Of course, the central axis CA of the enclosure 18 and the central axis CA of the vibrating element 4 may be offset and/or skewed without departing from the scope of the invention as described below and the independent definitions are specifically applied.

The lip 46 of the enclosure 18 may be spaced apart from the vibrating element 4 so that the lip 46 does not impede vibrations of the vibrating element 4. Of course, the lip 46 must be close to the vibrating element 4 so that surface tension prevents escape of the liquid. For example, the lip 46 may be spaced apart from the vibrating element 4 by less than 250 microns or less than 125 microns. The vibrating element 4 may not touch the enclosure 18 during vibration when the maximum amplitude is small enough to prevent contact. Stated another way, the lip 46 has a surface spaced apart from the vibrating element 4 less than 250 microns average, or less than 125 microns average, and is spaced apart from the vibrating element 4 for at least 270 degrees of total angular extent which does not contact the vibrating element 4. Stated yet another way, the surface is spaced apart by a separation distance of at least 125 microns around at least 270 degrees of the plurality of openings 6 when viewed along the central axis CA. The lip 46 may extend completely around the openings 6 without contacting the vibrating element 4 even during vibration for fluid delivery. The interface on either side may be interrupted rather than continuous without departing from the scope of the invention. For example, the surface of the lip 46 may contact the vibrating element 4 along four small sections which span 20 degrees each so that the lip 46 does not contact the vibrating element 4 along at least 270 degrees even though not continuous. As used herein, the chamber 16 is defined by the enclosure 18 and the vibrating element 4 so long as the fluid is prevented from escaping between the enclosure 18 and the vibrating element 4 and the chamber 16 shall be defined as the fluid retaining space even though the chamber 16 is not entirely enclosed. The term "lip" as used herein simply refers to the surface adjacent the vibrating element 4 and does not require any particular structure or shape and may simply be an end of the wall 44 or coating at the end of the wall 44. For example, the lip 46 may be wider like a flange, a rim of a rigid cup, or a rippled surface, undulating or sawtooth shaped surface without departing from the meaning of "lip" as used herein. Although the fluid may be held in the chamber 16 by surface tension along the lip 46 when the lip 46 is spaced from the vibrating element 4, the majority of the fluid may be free of capillary feed features as is sometimes used in the prior art. Such prior art systems that incorporate capillary feed typically do so along the fluid feed area immediately adjacent to the openings 6 in the vibrating element 4. As described below, the present invention may provide sufficient space adjacent to the openings 6 so that capillary action is not required or incorporated to deliver fluid to the openings 6.

The lip 46 may also be in contact with the vibrating element 4, rather than spaced apart, while not overly restraining the vibrating element 4 and still retaining the fluid. To this end, the lip 46 may be biased against the vibrating element 4 with a relatively low force. For example, the force exerted on the vibrating element 4 by the lip 46 may be less than 3 gram-force, and may be less than 2 gram-force, measured in a direction of the central axis CA of the enclosure 18 (and the vibrating element 4 as well). The lip 46 may also exert a controlled spring load on the vibrating element 4 with an average spring constant of no more than 60 gram-f/mm or even no more than 40 gram-f/mm for displacements up to 0.050 mm in the direction of the central axis CA. The controlled spring constant may aid in operation in extreme conditions which may affect interaction of the lip 46 and vibrating element 4 for extreme temperatures, pressures, and impact loads (dropped). The controlled spring constant may also aid in manufacturability in that manufacturing tolerances can affect the load ultimately exerted by the lip 46 on the vibrating element 4.

The lip 46 and/or the wall 44 may also be made of a resilient material for compliant contact between the lip 46 and the vibrating element 4 and the resilient material and geometry of the enclosure 18 may contribute to develop the spring force response. For example, the lip 46 may be made of a material having a durometer of less than 60 A. The wall 44 may have a thickness of 0.003 to 0.007 inch surrounding the chamber 16. The resilient nature of the enclosure 18 may be provided by the material of the lip 46 itself and/or mechanically with a tab, leaf spring, coil spring, cantilever, a resilient mounting for the container 17, or any other suitable mechanism or combination. For example, the enclosure 18 may be a rigid cup with an elastomer coating along the rim with an appropriate spring exerting a force on the cup in accordance with this aspect of the invention.

The wall 44 of the enclosure 18 includes a sidewall 56 which may also contribute, and in some cases the largest amount, to the resilient nature of the engagement with the vibrating element 4. The sidewall 56 extends from the lip 46 to the hub 35 and extends completely and around the central axis CA. The resilient nature of the enclosure 18 may be provided for in whole or part by the shape of the sidewall 56. The sidewall 56 may have a tapered portion 60 extending from a large end (diameter of 0.210 to 0.220 inch) to a small end (diameter of 0.180 to 0.190 inch) with the large end positioned nearer to the vibrating element 4 (and may be adjacent the lip 46 at the distal end) and surrounds and encompasses a larger area than the small end. The tapered portion 60 of the sidewall 56 may also include a first frustoconical portion 62 extending from the lip 46 and a radial extension 64 extending primarily radially inward from the small end of the first frustoconical portion 62 to the hub 35. The radial extension 64 extends radially inward with respect to a central axis CA of the enclosure 18. The orientation and relative dimensions of the parts of the wall 44 and sidewall 56 are described herein with reference to a cross-sectional shape at a plane on which the central axis CA (of the vibrating element 4 and/or the enclosure 18) lies for a total angular extent of at least 270 degrees when viewed along the central axis CA (or completely around the central axis CA as shown). The radial extension 64 extends radially inward at least 20% of an equivalent radius of the open end. The radial extension 64 may have a ratio of radial to longitudinal displacement of at least 3 to 1 relative to the central axis CA with the central axis CA representing the longitudinal direction and may be positioned 0.014 to 0.030 inch or 0.014 to 0.040 inch from the vibrating element 4 measured along a central axis CA. As used herein, "equivalent radius" or "equivalent diameter" refers to the radius or diameter of a circle having the same area. The tapered portion 60 of the sidewall 56 has a second frustoconical portion 63 extending from the radial extension 64 to the hub 35.

The tapered portion 60 of the sidewall 56 extends from the lip 46 to the hub 35. In total, the tapered portion 60 may have a radial to longitudinal displacement ratio of at least 1 to 3, at least 2 to 3 or at least 1 to 1 relative to the central axis CA. As used herein, "tapered" does not require a gradual or continuous change and only refers to a reduction in size perpendicular to the central axis CA which represents a feed area. The reduction may be stepped or may extend substantially only radially inward like the radial extension 64 without departing from the definition of "tapered" as used herein. The tapered portion 60 of the sidewall 56 may extend radially (relative to the central axis CA of the enclosure 18) at least 20% of an effective radius of the enclosed boundary of the lip 46 around at least 270 degrees (and may extending completely and fully around the central axis CA) of the enclosure 18 when viewed along the central axis CA. The tapered portion 60 of the sidewall 56 may have a thickness of 0.003 to 0.007 inch and may be about 0.005 inch to enhance the flexibility of the sidewall 56. The sidewall 56 extends to the hub 35 and a connector 66 is formed which engages an end of the tube 56 (FIG. 7) having a mating connector (not shown). The main inlet 52 is formed by the hub 35 which receives the fluid from the lumen 54 in the tube 56. The other end of the lumen 54 in the tube 56 receives fluid from the pump 32.

The lip 46 may be unattached to the vibrating element 4 while still being in contact with the vibrating element 4. The terms "no attachments", "not attached" or "unattached" as used herein means no connection other than frictional contact. Stated another way, the lip 46 may be free to move away from the vibrating element 4 along the central axis CA. Stated still another way, the enclosure 18 (specifically the lip 46) is unattached to have a degree of freedom in the direction of the central axis CA relative to the vibrating element 4. Thus, the lip 46 and the vibrating element 4 may have channels and/or raised baffles or walls which may restrain lateral movement do not constitute an "attachment" as defined herein. The lip 46 may have a curved surface with a radius of curvature of about 0.005 inch to provide a rounded edge to the lip 46.

The vibrating element 4 and lip 46 define an enclosed border 41 at the interface of the two (while each one may define the enclosed border 41 by itself in that they define the same boundary with one another). The enclosed border 41 defines an enclosed feed area 51 (FIG. 11) at the fluid side of the vibrating element 4 which may be 5.3-5.7 mm or about 5.5 mm in diameter. The openings 6 in the vibrating element 4 encompass and define a delivery area 39 of the vibrating element 4 which is circular and has a diameter of 2.6 to 3.0 mm or stated another way of less than 3.0 mm or about 2.8 mm. Of course, other patterns and shapes other than circular may be used with the effective diameter or radius for comparison. The enclosed border 41 may be appreciably larger than the delivery area 39 in that the delivery area 39 may be no more than 75%, or no more than 50%, of the enclosed feed area 51. Stated another way, the enclosed feed area 51 may be at least 30% larger, and may be at least 100% larger, than the delivery area 39. Stated yet another way, the enclosed feed area 51 may be larger than the delivery area 39 so that an excess feed area 58 (defined by the enclosed feed area 51 not coextensive with the delivery area 39 when viewed along the central axis CA) is at least 30% of the delivery area 39 and may even be larger than the delivery area 39 or even up to 50% larger. The excess feed area 58 may be an annular ring for a concentric arrangement or crescent shaped for offset circular areas (which may be non-circular but represented and compared as circles when using equivalent radius or diameter). The delivery area 39 of the vibrating element 4 defines a geometric center and an effective radius for a circle of equivalent area. The enclosed feed area 51 also defines a geometric center and an effective radius for a circle of equivalent area. The geometric center of the enclosed feed area 51 may be above the geometric center of the delivery area 39 and offset by at least 0.3 times the effective radius of the delivery area 39. The fluid held in the chamber 16 also defines a geometric center positioned less than 0.015 inch from the vibrating element 4 when measured in the direction of the central axis CA. The geometric center of the fluid may similarly be positioned at least 0.3 times the effective radius of the delivery area 39 above the geometric center of the delivery area 39 for an offset design. For a concentric embodiment, the geometric center of the fluid (or the volume of the chamber 16) is less than 0.1 times the effective radius of the delivery area 39 from the central axis CA of the vibrating element 4.

Although the enclosure 18 provides a relatively small chamber 16 with a small volume, the chamber 16 may provide fluid to the openings 6 without requiring capillary feed as some prior art teaches. The enclosure 18 has an internal surface 49 which defines the boundary of the chamber 16 as defined by the enclosure 18. The fluid is held in the chamber 16 in contact with the internal surface 49. An internal wall 45 of the enclosure 18 has a side 47 facing the openings 6 which is spaced apart from the openings 6 by a separation which may be about 0.017 inch. The spacing between the internal surface 49 of the enclosure 18 and the vibrating element 4 may be larger than a capillary spacing so that capillary action is not present. Capillary feed may impede fluid flow when it is desired to deliver the fluid quickly and also makes it difficult to completely deliver from the feed system which presents residual fluid problems. To avoid possible capillary action and/or minimize obstruction to flow it may be desirable to have a minimum spacing between the openings 6 and the nearest part of the enclosure 18 so that at least 75%, or at least 95%, or even all, of the openings 6 have a minimum spacing of at least 0.010 inch, or at least 0.014 inch to the nearest part of the internal surface 49 of the enclosure 18.

While it may be desirable at times to avoid capillary action, it is still desirable to provide for quick delivery of substantially all of the fluid and, thus, the enclosure 18 may still be shaped so that the fluid in the chamber 16 doesn't need to travel far to reach the openings 6 for ejection. To this end, the internal surface 49 of the enclosure 18 may be shaped so that at least 75%, or at least 95% or even all, of the fluid in direct fluid communication with the fluid in the chamber 16 is no more than 0.060 inch, or no more than 0.040 inch, from the nearest opening 6 in the vibrating element 4. Stated another way, the chamber 16 may be shaped and formed by the internal surface 49 of the enclosure 18 so that at least 75%, 95% or even all of the fluid in the chamber 16, and optionally all fluid in fluid communication with the fluid in the chamber 16, has direct line of sight to the nearest opening 6. Many prior art systems have wet feed tubes or conduits which are filled with liquid and are spaced much further than 0.060 inch from the openings 6 and must overcome surface tension and other forces which may tend to hold the fluid in the conduits which may contribute to residual volume. Thus, in some instances it may be desirable to have most, if not all, of the openings 6 separated a minimum distance from the enclosure 18 to avoid capillary action while at the same time still having all of the fluid relatively close to the openings 6 and without impediment for rapid, substantially complete delivery in a short period of time and with low residual volume. When addressing both concerns, the enclosure 18 forming the chamber 16 may be spaced apart by 0.014-0.040 inch from all of the openings 6 when viewed and measured in the direction of the central axis CA of the vibrating element 4. "Fluid in communication" with another fluid refers to fluid that is continuous which includes feed tubes, pipes, wicks and channels which feed fluid to the openings.

The enclosure 18 may be an integrally formed structure which defines the chamber 16. The integrally formed structure may be made of a thermoplastic elastomer and formed by a suitable method such as injection molding. One example is sold under the name Thermolast® supplied by Kraiburg as TFSCGN which is a thermoplastic elastomer.

The volume of fluid delivered may fill the chamber 16 only 75-90% full which may provide room during delivery to encourage all of the fluid to gather in the chamber 16 due to surface tension forces. Delivering the fluid at a velocity of at least 0.5 m/s (or at least 1.0 m/s) to the enclosure 18 may also encourage substantially all of the fluid ejected from the tube 56 to collect in the chamber 16 rather than being left behind as residual. Stated another way, the pump delivers the fluid at a pressure of at least 200 psi (and may be about 300 psi) which may be sufficient to achieve the velocities desired for many fluids delivered to the eye. In this manner, the small fluid amount remains a single fluid "droplet" which is fired into the enclosure 18.

The enclosure 18 may split the flow from the main inlet 52 into a first inlet 55 and a second inlet 57 each leading to the chamber 16. The enclosure 18 may also have a third inlet 59 and a fourth inlet 61 and all aspects of the first and/or second inlets 55, 57 are expressly incorporated for the third and/or fourth inlets 59, 61 and the other of the first and second inlets 55, 57 when discussed independently and all such features and limitations are expressly incorporated for all of the other inlets. The first inlet 55 directs the fluid at the internal surface 49 of the enclosure 18, such as the tapered portion 60 of the sidewall 56, before being directed at the openings 6 in the vibrating element 4. The first inlet 55 and the second inlet 57 may lead directly to the chamber 16 with the inlets both being oriented to direct all of the fluid entering the chamber 16 (or at least 90% of the fluid) at the internal surface 49 of the enclosure 18 (such as the internal surface 49 along the sidewall 56) before being directed to the openings 6 in the vibrating element 4. In this manner, the possibility that the fluid is forced through the openings 6 during filling of the chamber 16 may be reduced. In particular, when the fluid is forced into the chamber 16 at a velocity or pressure as suggested herein it may be advantageous to direct the fluid into the enclosure 18 in this manner.

The main inlet 52 initially directs the fluid at the internal wall 45 opposing the openings 6 which forms part of a flow splitting chamber 66. The internal wall 45 extends from one side of the sidewall 56 to the other relative to the central axis CA to form the inlets. The flow splitting chamber 66 splits the flow into four streams that pass through the four inlets each spaced apart from and directed at the tapered portion 60 of the sidewall 56. The flow splitting chamber 66 may lead directly to the chamber 16 as shown or may have additional baffles or flow altering features. The main inlet 52 directs the flow in a direction within 30 degrees of the central axis CA of the enclosure 18 and may be along and aligned with the central axis CA as shown. The first inlet 55 and the second inlet 57 may be oriented to direct the fluid within 30 degrees of perpendicular to the central axis CA to avoid fluid being directed at the openings 6. The enclosure 18 may have a third inlet and a fourth inlet which are also oriented at the sidewall 56 of the enclosure 18. When viewed along the central axis CA of the enclosure 18, the adjacent inlets are oriented 60-120 degrees from one another and may be about 90 degrees from the adjacent inlets 55, 57, 59, 61 as shown.

The flow splitting chamber 66 has a cup-shaped wall 68 (which includes the internal wall 45) with a concave side 70 facing toward from the vibrating element 4. The cup-shaped wall 68 has all four inlets formed therein. The cup-shaped wall 68 extends radially outward from a central axis CA of the enclosure 18 for at least 25% of an effective radius defined by the lip 46 for an angular extent of at least 240 degrees relative to the central axis CA of the lip 46. The first inlet 55 has a radial dimension and a longitudinal dimension relative to the central axis CA with a ratio of the radial dimension to the longitudinal dimension being 0.5 to 1.5. The first inlet 55 and the second inlet 57 extend radially inward toward the central axis to expose some of the main inlet 52 when viewed in the direction of the central axis CA, however, direct longitudinal flow from the main inlet 52 to the vibrating element 4 is prevented by the radial component to the flow which is created by the bulk of the fluid directed radially outward by the internal wall forming the bottom of the cup 68.

The chamber 16 is also formed so that at least two, three or four inlets 55, 57, 59, 61 are provided which, together with the dimensions of the chamber 16, provide a lower energy state to encourage the fluid to collect in the chamber 16 rather than any residual part of the fluid remaining in the splitting chamber 66 or extending between the chamber 16 and the flow splitting chamber 66. Although many aspects of the present invention are directed to minimizing residual fluid, the present invention may be practiced with some residual volume left and, in fact, some aspects the invention may be used with a wet system without departing from those aspects of the invention.

As fluid is evacuated (ejected through the openings 6) from the chamber 16 make-up air must be introduced to vent the chamber 16 during operation. The enclosure 18 may vent air into the enclosure 18 between the lip 46 and the vibrating element 4 with the lip 46 separating sufficiently from the vibrating element 4 during vibration to vent air into the enclosure 18 without releasing fluid. Air vented between the lip 46 and the vibrating element may aid in fluid delivery by moving or displacing fluid at radially outer regions radially inward toward the openings 6 and by simply occupying these radially outer spaces (excess feed space) rather than residual fluid which might occupy this space.

Air may also be drawn into some openings 6 of the vibrating element 4 to vent the enclosure 18 as fluid is ejected through the openings 6. The air is introduced as small bubbles in the chamber 16 which may distribute the fluid among in some sense to find "active" ejection openings 6. The enclosure 18 may include no other vent openings, or no dedicated vent, which simplifies the system and eliminates one possible contamination path or source. Of course, a dedicated vent may be provided for the chamber 16 without departing from the invention as now described.

Referring to FIGS. 32-35, another chamber 16A and enclosure 18A are shown which are substantially the same as the chamber 16 and the enclosure 18 and all uses and combinations and all other disclosure related to the chamber 16 and the enclosure 18 (and all other enclosures and chambers described herein) are incorporated here. Likewise, all discussion for chamber 16A and enclosure 18A are also incorporated for the chamber 16 and the enclosure 18 (and all others). The enclosure 18A has a wall 44A with a lip 46A adjacent the vibrating element 4 (see FIG. 2). A wall opening 124 is formed in the wall 44A to vent the chamber 16A during operation. The wall opening 124 may also have dimensions which enhance the flexibility of the enclosure 18 as described below. The lip 46A may have a PTFE coating 120 adjacent to the vibrating element 4 to reduce friction therebetween. The vibrating element 4 may similarly have a PTFE coating 122 adjacent to the lip 46 to reduce friction therebetween. The coatings 120, 122 may extend around at least 270 degrees when viewed along the central axis CA. Of course, the coating 122 may extend entirely around the central axis CA. An inner surface 123 of the enclosure 16, 16A may be hydrophobic (coated or by virtue of the material property) over at least 70% of the inner surface 123 of the enclosure 18A in contact with the fluid loaded prior to delivery.

The wall opening 124 may take any suitable shape such as a wedge-shaped opening. The wall opening 124 extends through the wall 44A, specifically a sidewall 56A portion of the wall 44A, to expose the chamber 16A. The wall opening 124 may also form a small gap 131 in the lip 46A, which together with the geometry of the opening 124, is small enough to prevent fluid leakage but may still be large enough to vent the enclosure 18A by permitting air to enter when fluid is ejected. All discussion and applications concerning venting of the enclosure 18 are incorporated here such as discussion of venting between the lip 14 and the vibrating element 4, spacing between the lip and vibrating element and the force-displacement characteristics. Thus, the lip 14A may be in contact with the vibrating element 4 or spaced apart in any manner described herein.

The wall opening 124 has a longitudinal dimension 126 measured from the lip 46 in the direction of the central axis CA and a radial dimension 128 measured in a radial direction relative to the central axis CA. The longitudinal dimension 126 of the wall opening 124 is at least 80% of a separation 125 between the vibrating element 4 and a side 47A of the enclosure 18A facing the openings 6 and may extend substantially the entire length as shown. The radial dimension 128 of the wall opening 124 is not more than 10%, or no more than 5%, of an equivalent circumference of the lip 46A. The radial dimension 128 may be about 0.025 inch while the longitudinal dimension 126 may be about 0.022 inch. The dimensions of the enclosure 18A, the wall 124A and the chamber 16A may be any suitable dimensions including those associated with the enclosure 18 and all geometric relationships all of which are incorporated here.

The wall opening 124 extends from the lip 46A proximally and may increase the flexibility of the enclosure 18A due to its position and shape. The wall opening 124 has a circumferential dimension 130 measured in a circumferential manner relative to the central axis CA. The circumferential dimension 130 may be about 0.012 inch at the lip 46A (same as the gap 131) and tapers so that the two sides converge at a proximal end 132 of the wall opening 124. The circumferential dimension 130 is defined herein as a measurement for a line segment that is perpendicular to a radial orientation of the central axis CA. The wall opening 124 tapers down as the wall opening 124 extends proximally from the lip 46A. The wall opening 124 tapers so that a tapered shape 132 of the wall opening 124 is oriented in the direction of ("points at") at least one of the inlets 55, 57, 59, 61 to the chamber and may be oriented to align with two inlets when viewed along the central axis CA. Orienting the tapered shape 132 of the wall opening 124 with the inlet(s) 55, 57 in this manner increases flexibility since the inlet(s) and wall opening 124 cooperate to increase flexibility given their geometric alignment. The "orientation" of the tapered opening shall be defined as the bisection of the tapered angle extending away from the wall opening 124. The tapered shape 132 is also within 10 degrees of a radial orientation relative to the central axis CA and may be substantially radially oriented as shown. The wall opening 124 is also positioned along a frustoconical portion 62A with the wall opening extending proximally from the lip for at least 80% of the length of the frustoconical portion 62A.

The pump 32 is now described in more detail. The pump 32 draws discrete volumes from the fluid container 17 and delivers these volumes to the chamber 16. The fluid container 17 may be any other suitable mechanism such as a piston/plunger associated with the fluid container 17 in some applications. The fluid container 17 may have a fluid carrying capacity which is at least 150 times the volume of the chamber 16 (or the volume of the fluid delivered) for a multi-dose device. The pump 32 may be configured to deliver the same (and optionally the only) volume each time. Of course, a variable volume pump 32 may also be used without departing from virtually all aspects of the invention.

The present invention may be used to provide single dose delivery with substantially the whole dose delivered thereby leaving little residual fluid in the chamber 16. The vibrating element 4 may deliver the fluid from the enclosure 18 so that no more than 5%, or no more than 2%, of a total volume of the chamber 16 is occupied by residual fluid (from a previous fluid delivery) or less than 1 microliter remains. Stated another way, the vibrating element is operated to dispense substantially the entire volume of fluid in communication with the openings 6 so that no more than 5%, or no more than 2%, of the fluid volume (or less than 1 microliter) remains in the chamber 16 after the fluid is ejected and a single actuation for fluid ejection. In this manner, the chamber 16 is substantially empty after a single application of the fluid (a single firing actuation). An advantage of some aspects of the present invention over other fluid delivery systems is that the chamber 16 receives a single dose that is nearly completely delivered to leave the chamber 16 substantially dry and free of residual fluid between activations. Contamination and degradation of the fluid may be reduced compared to "wet" systems that maintain the fluid in contact with the vibrating element 4 between uses or which have incomplete delivery.

The enclosure 18 may be sized so that the enclosure 18 may be at least 70-95% full with the fluid volume as mentioned above which may help the fluid to gather in the chamber 16 as a single droplet. The chamber 16 may define a relatively small volume such as less than 14 microliters or 10-14 microliters. The fluid volume may be 7-12 microliters or 10-12 microliters. The lumen 54 in the tube 56 delivers the fluid through the main inlet 52 to the enclosure 18 with the main inlet 52 having a diameter of 0.040 to 0.060 inch and may be about 0.054 inch, The flow splitting chamber 66 may have a diameter which essentially matches the main inlet 52 of about 0.054 inch. The tube 56 extends from the main inlet 52 and may have a volume of less than 2 microliters to further minimize residual fluid. The tube 56 may be part of the enclosure 18 and may be formed with the enclosure 18 rather than as separate parts.

In use, fluid delivery to the eye may also be relatively rapid to reduce the likelihood of interference from a blink during delivery. The fluid delivery may take less than 200 ms and may even be less than 150 ms or even 100 ms. The vibrating element 4 may also be operated with a pause between periods of vibration during a single actuation. For example, the vibrating element may be driven by the piezoelectric element 15 for a first period of operation of about 26 ms with a pause of about 3.65 ms followed by a second period of operation of about 26 ms. The vibrating element 4 may be driven by the piezoelectric element 15 with two pauses with the piezoelectric element 15 being energized or activated for a first period of time, a second period of time and a third period of time with the first and second periods separated by the first pause and the second and third separated by a second pause in driving vibration of the vibrating element 4. The first and second pauses in driving vibration may be 0.5 ms to 4.0 ms. Each of the first, second and third time periods may be 20-40 ms and the overall time of delivery may be less than 150 and even less than 100 ms and may be about 85.3 ms. Each of the first, second and third periods of vibration may be further subdivided into periods of activation for about 816us and deactivated for about 586us for the piezoelectric element 15. During the deactivated time, the vibrating element 4 may continue to vibrate and eject fluid although not being actively driven by the piezoelectric element 15. Similarly, during each pause in activation of the piezoelectric element 15 the vibrating element 4 may continue to eject the fluid. The "pause" may be defined as a continuous deactivation of at least 2% of the total time and the total pause time for a plurality of pauses being at least 6% and may be about 8.5% of the total delivery time. The deactivated times are defined distinct from the pause in that the pause is at least 2% of the time continuous while the deactivated time is shorter and may be defined as a continuous time of 0.5-1.0% of the total delivery time and a total of the deactivated times being at least 30% of the total delivery time. Stated another way, the deactivated time is a continuous time of 2.0 to 2.5% of the first period of time (and second and third as well) and a total deactivated time of at least 30% of the first period of time. Of course, the delivery times are defined to illustrate the invention and the activation times and patterns may change depending on the surface tension of the ejected fluids.

As mentioned above, the frequency of the alternating signal used to activate the piezoelectric element 15 and subsequently activate and vibrate the vibrating element 4 is induced at a drive frequency of 100 kHz to 160 kHz. Furthermore, the frequency is selected by the control system 11 as a randomized frequency centered about the drive frequency (ranging from 100 kHz to 160 kHz) for each of the plurality of activations during a single delivery and may be randomized at least 20 and may be at least 40 times. Stated another way, the vibration frequency is changed (randomly in a manner centered on the drive frequency) on average at least 33 times for a single firing actuation so that the piezoelectric element 15 is driven at a frequency for no more than 3% of the delivery time (average) before being changed. It is believed that the chaotic nature of the randomization of the drive signal may aid in ejecting fluid. The randomized nature may be provided by a predetermined randomized set of values which are applied to the centered operating frequency or the randomized values uniquely generated by the control system 11.

The vibrating element 4 may also be designed to vibrate with a relatively low maximum amplitude. For example, the vibrating element 4 may vibrate with a maximum amplitude of less than 2 microns, less than 1.5 microns or within a range of 0.5-1.5 microns, 0.8-1.2 microns or may be about 0.8 microns. The maximum amplitude of the vibrating element 4 may also be relatively small compared to the size of the openings 6 in the vibrating element 4. For example, the maximum amplitude may be no more than 5%, or no more than 3%, of an effective diameter of the cross-sectional shape of the openings 6 at the delivery side. For example, when the maximum amplitude is 1.0 microns and the average diameter of the openings 6 at the delivery side is 40 microns the maximum amplitude is only 2.5% of the average diameter or about 2.5% of the average diameter of the fluid droplets ejected. The maximum amplitude also represents a relatively small amount compared to the thickness such as no more than 5.0% or even no more than 3.0% of the thickness of the vibrating element 4 (measured from the fluid side to the delivery side). As used herein, the thickness may be an average thickness for the area bounded by the openings 6. Operation at low amplitude may also contribute to venting through the openings 6 in that air may be admitted through some of the openings 6 having even low displacements. Operation at low amplitude may also help maintain fluid containment between the lip 46 and the vibrating element 4. When the lip 46 is spaced apart from the vibrating element 4, the lip 46 may be spaced apart an average distance greater than the maximum amplitude of the vibrating element 4 during vibration. Stated another way, the maximum amplitude is less than an average separation distance between the surface of the lip 46 and the vibrating element 4.

Figure 13:
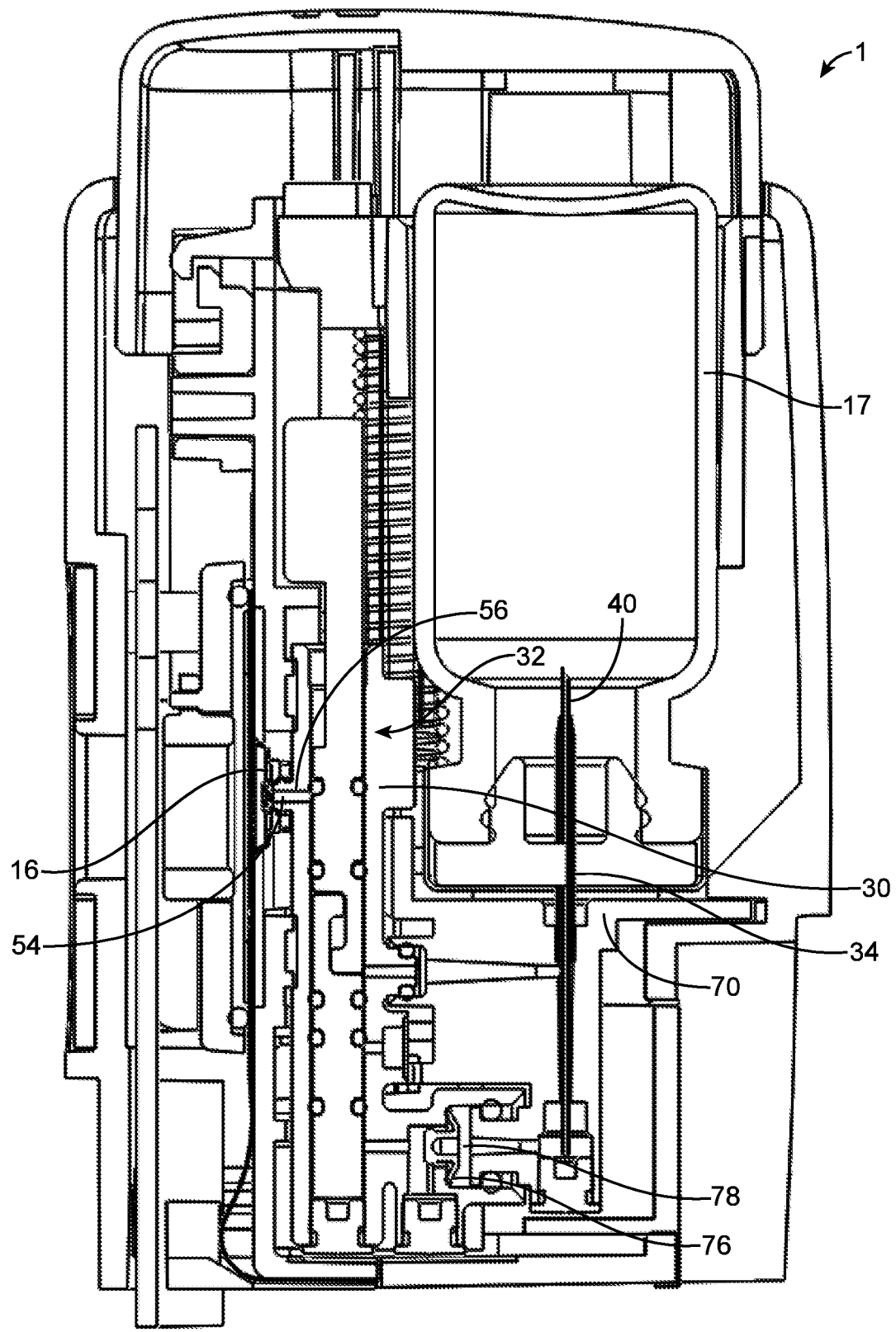
FIG. 13 shows a cross-sectional view with the device in a stored position.
Figure 14:
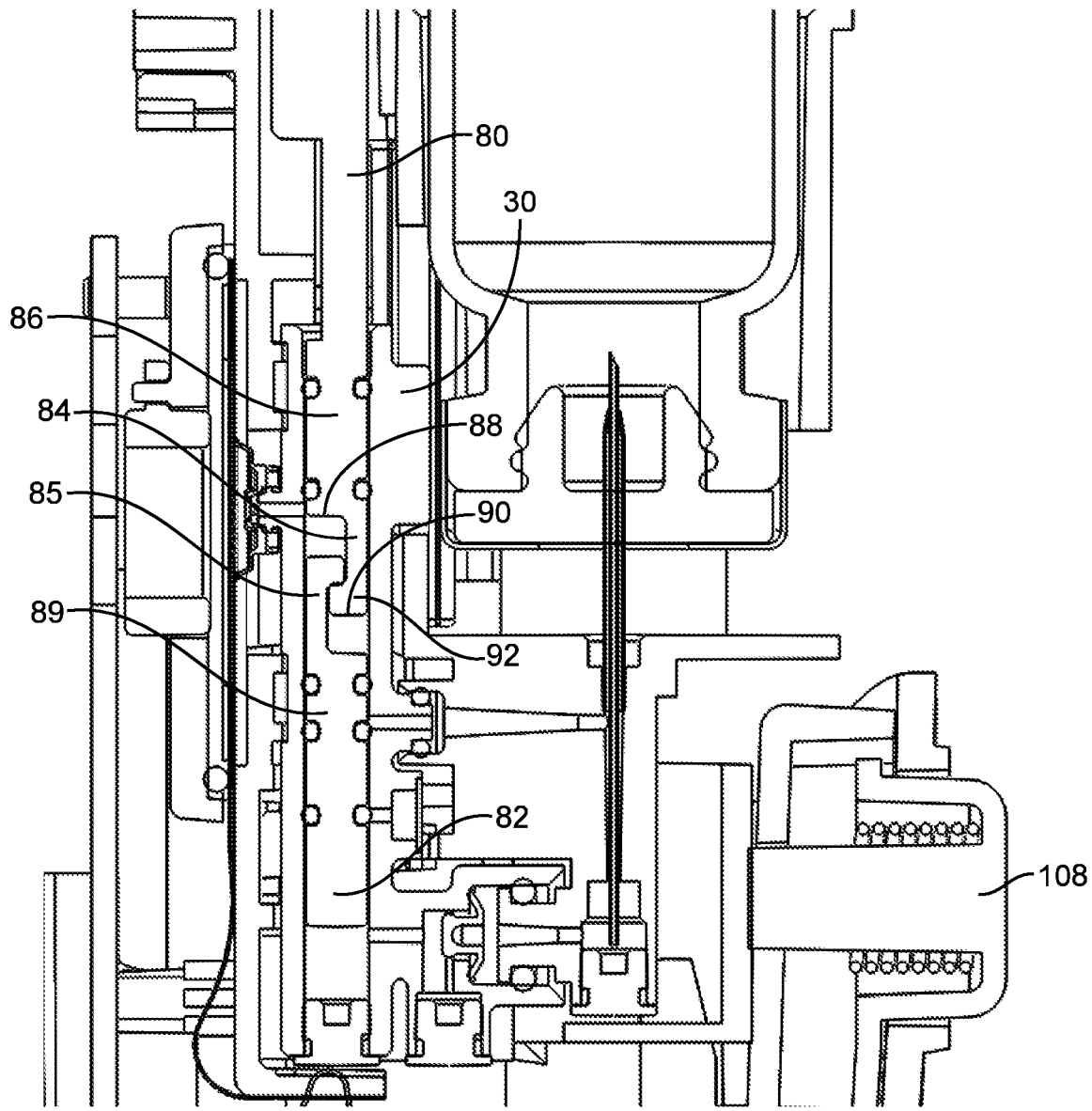
FIG. 14 shows the pump advanced during the forward stroke with fluid contained in pump.
Figure 15:
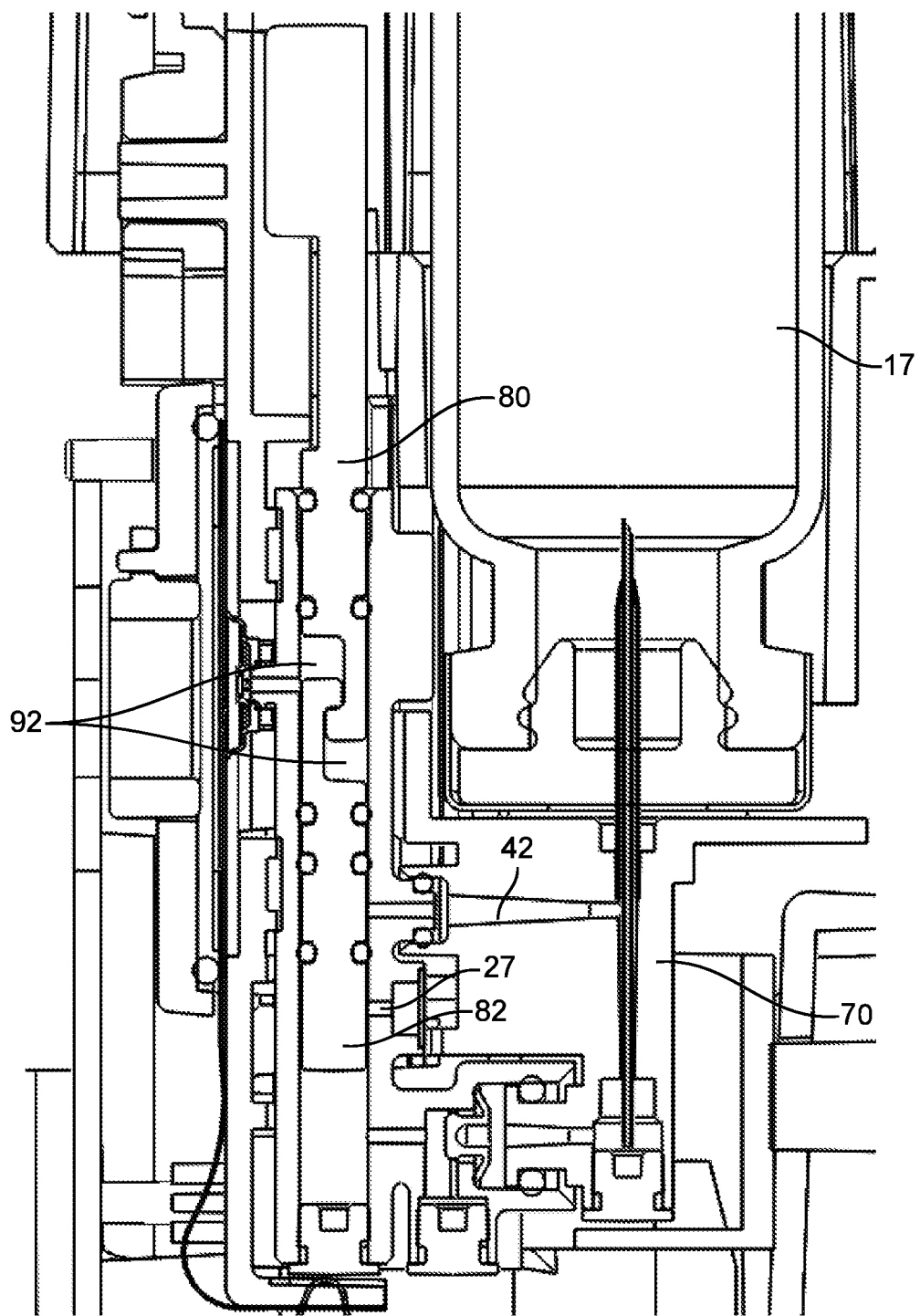
FIG. 15 shows the pump at full forward stroke.

Referring to FIGS. 13-17, the housing is partially removed to expose the pump 32. The pump 32 delivers fluid from the fluid container 17 to the chamber 16 through the lumen 54 in the tube 56 and through the main inlet 52 (see FIG. 12). The fluid container 17 may be any suitable container such as a vial, ampoule, bag, bladder or a fixed container that is filled without departing from the scope of the present invention. Similarly, the pump 32 may be any suitable mechanism for delivering the fluid to the enclosure 18 without departing from various aspects of the invention. The fluid container 17 has a pierceable cap 70 which is pierced by a delivery needle 34 and the vent needle 40. The delivery needle 34 defines part of a delivery flow path and the vent needle 40 defines part of a vent path. The delivery flow path extends to the pump 32 and from the pump 32 through the tube 56 and the main inlet 52 into the chamber 16. Referring to FIGS. 3 and 13, the delivery needle 34 and the vent needle 40 are mounted to a container support 70 on which the container 17 is mounted. The container support 70 has a coupling 72 which engages the manifold 30. A vent lumen 73 includes a one-way valve 76, such as an umbrella valve 78, which permits air into the fluid container 17 to make up for the volume of fluid lost as explained below.

The pump 32 has a first part 80 and a second part 82. The first part 80 reciprocates between a stored position (FIG. 13) to a partial stroke position (FIG. 14) and to a forward stroke position (FIG. 15) at the greatest displacement. The first part 80 returns to the stored position to complete a cycle which delivers a volume of fluid to the chamber. The second part 82 also reciprocates between a stored position to a forward stroke position at a greatest displacement and back to the stored position each cycle. The first part 80 has an extension 84 extending from a main body 86. The main body 86 has an end 88 facing an end 90 of a main body 89 of the second part 82. The extension 84 on the first part 80 extends toward and interlocks with an extension 85 extending from the main body 89 of the second part 82. The first part 80 is driven and in turn drives the second part 82 through each cycle by engagement of the extensions 84, 85 and/or the ends 88, 90 of main bodies 86, 89 with one another. A cavity 92 is formed between the first part 80 and the second part 82 with the size of the cavity 92 changing as the first and second parts 80, 82 move toward and away from one another. The cavity 92 increases in size when the first and second parts 80, 82 move away from one another which draws fluid into the cavity 92 during the forward stroke. The cavity 92 decreases in size when the first and second parts 80, 82 move toward one another which delivers the fluid from the cavity 92 to the chamber 16 during the return stroke. The cavity 92 has a volume commensurate with volume of the fluid being delivered which may be 7-12 microliters.

The fluid is drawn into the cavity 92 during the forward stroke of the first part 80. The first part 80 and the second part 82 are movable from a stored position of FIG. 13, to the partial forward stroke position of FIG. 14 and finally to the full forward stroke position of FIG. 15. The first and second parts 80, 82 move to the full stroke position with the first part 80 pulling the second part 82 upward due to the interlocking extensions 84, 85 engaging one another. In the full forward stroke position the pump 32 is ready to deliver the fluid through the tube 56 and into the enclosure 18.

Figure 16:
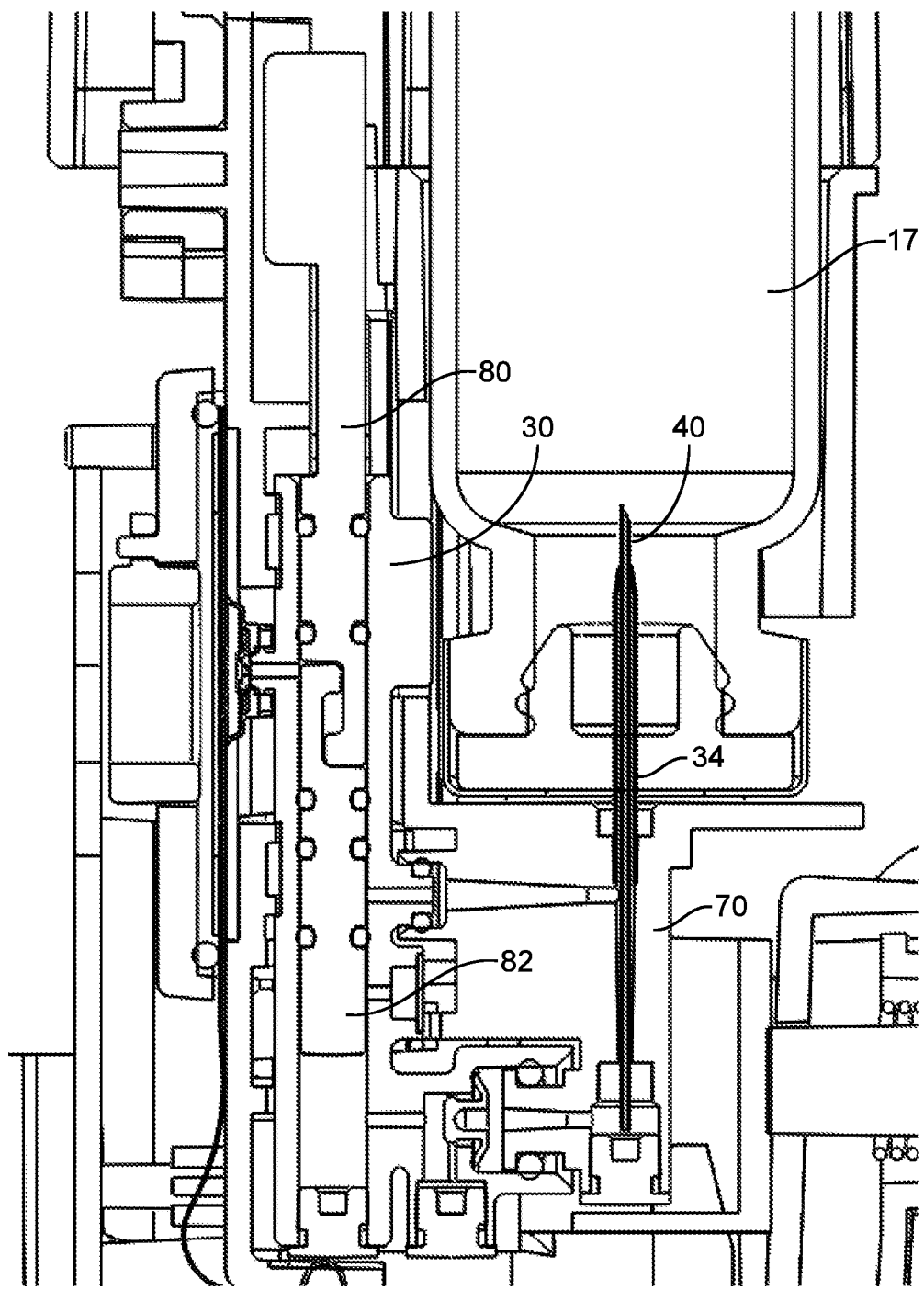
FIG. 16 shows the pump at the end of fluid delivery through the tube and into the enclosure.
Figure 17:
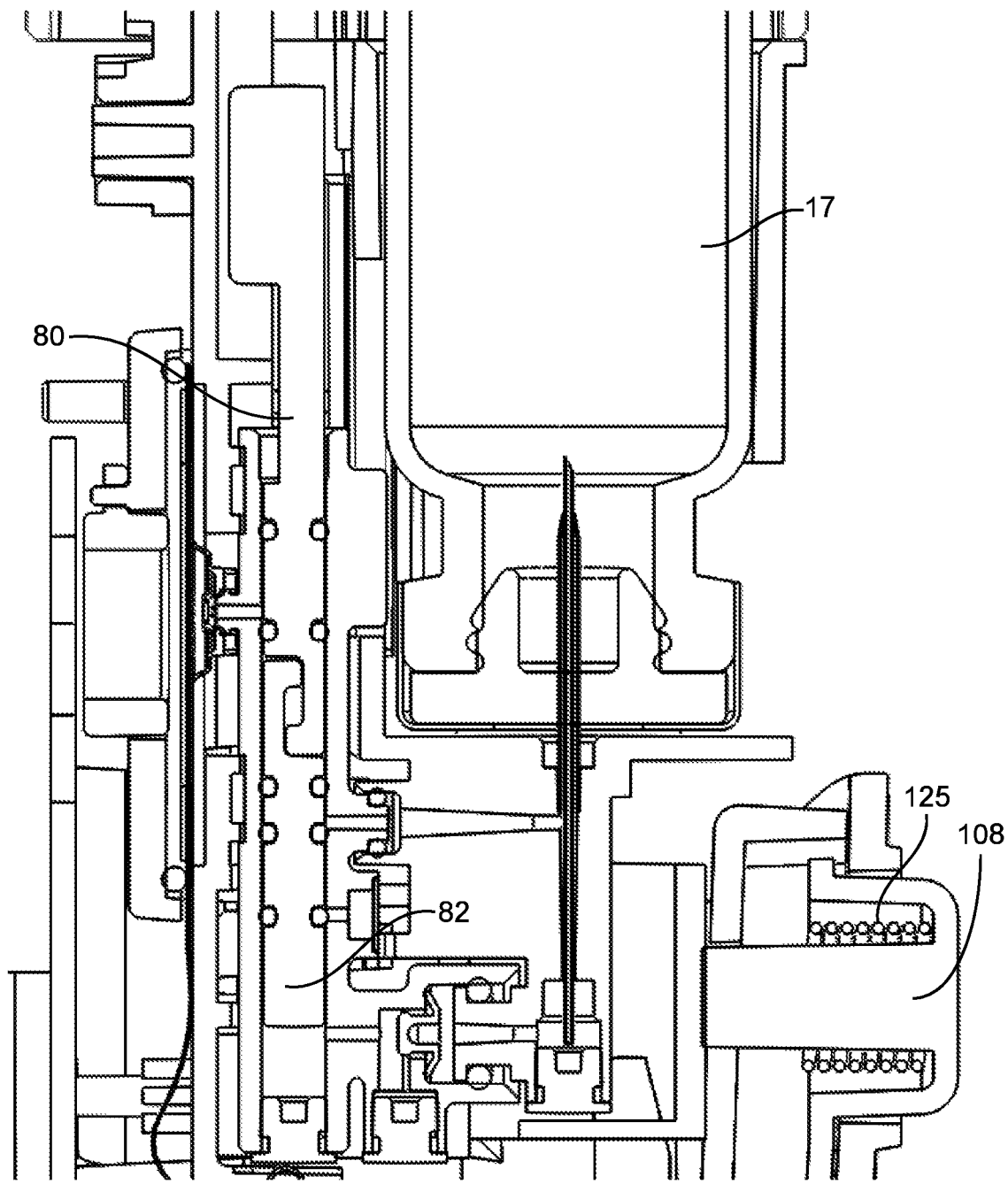
FIG. 17 shows the pump during the return stroke.

When the first and second parts 80, 82 reach the partial stroke position of FIG. 16 during the return stroke the fluid has been delivered from the cavity 92 to the chamber 16. The first and second parts 80, 82 complete the cycle by moving to the partial reset position of FIG. 17 and to the fully reset position of FIG. 13 again. An additional optional step may be to purge any fluid left downstream of the chamber 16 with a separate displacing medium. The tube 56, the chamber 16 and the flow splitting chamber 66 represent a total downstream volume which is substantially free of fluid prior to delivery of the fluid. The volume of fluid delivered by the pump 32 may be 40-70% of the total downstream volume so that the tube 56 and flow splitting chamber 66 can be substantially empty when the fluid has been delivered to the chamber 16. As mentioned above, the fluid may be ejected at a relatively high velocity of at least 0.5 m/s (or with the pump delivering the fluid at a pressure of at least 200 psi) to "fire" the droplet into the chamber 16 and which may permit surface tension forces to gather and hold the small volume of fluid together.

The pump 32 may also deliver make up air into the container 17 to make up for the volume of fluid lost. The pump 32 draws air into a make-up chamber 94 during the forward stroke and forces the air from the make-up chamber 94 toward the fluid container 17 so that air enters and vents the fluid container 17 during the return stroke. The first and second parts 80, 82 each have an opposing end 97 positioned opposite the ends 88, 89 which face each other to form the cavity 92. At least one of the opposing ends 97 of the first and second parts 80, 82 may forms part of the make-up chamber 94 (such as the opposing end 97 of the second part 82) so that movement through a full cycle also draws air into the make-up chamber 94 during the forward stroke and expels air during the return stroke. Air is forced through the one-way valve 76, through the vent needle 40 and into the container 17 to make up for the volume of fluid lost (delivered). When the first and second parts 80, 82 reach the fully reset position the make-up air has been delivered and the pump 32 is in the stored position again with the first part 80 of the pump 32 blocking the main inlet 52 to the enclosure 18. O-rings are used to seal junctions and spaces between the first and second parts and the manifold and along the vent and fluid delivery paths.

Referring to FIGS. 4, 6 and 18-23 together, a drive mechanism for the pump 32 is shown. The drive mechanism includes the first actuator 94 (which may be a button 95) coupled to a first side 96 of a lever 98. The lever 98 rotates about pivot P in the direction of arrow A as the button moves downward. A second side 100 of the lever 98 is coupled to a support plate 102 of the first part 80 of the pump 32 so that the first part 80 moves upward with the first side 96 of the lever 98 from the stored position of FIGS. 18 and 21 to the forward stroke position of FIGS. 19, 20 and 22 in which fluid has been drawn into the cavity 92. The lever 98 may provide a mechanical advantage of about 11/6 due to the difference in lever arm length. Of course, a powered system using the battery 19 may also be used to move the fluid without departing from other aspects. A ratchet 104 prevents back-travel as the button 95 is depressed until reaching the necessary downward displacement (full forward stroke) at which point the ratchet 104 is released to permit the return stroke.

The first actuator 94 (such as the button) also loads the pump return spring 95 (and may load two pump springs 95) during the forward stroke. The loaded pump return spring(s) 95 drives the pump 32 back to the default or stored position during the return stroke. The pump return spring 95 may act on the first actuator 94, the lever or directly on part of the pump 32 itself such as on the first part 80 as shown. The first actuator 94 (button 95) is also returned to the stored position. In the stored position the main body of the first part 80 blocks flow through the lumen 54 in the tube 56 and the main body of the second part 82 blocks the vent path and the fluid delivery path. In this sense, the pump 32 acts a valve 104 and the present invention may be practiced with a dedicated valve closing the lumen 54 to the tube 56 and fluid being moved in another manner without departing from various aspects of the present invention.

Referring to FIGS. 25-31, the device 1 also includes a shutter 105 having an aperture 107 through which the fluid is delivered. The shutter 105 blocks and covers the vibrating element 4 in the stored position and may serve as an "off" switch (or defines the "off" condition) when using a position sensor 110 to detect the position of the shutter 105 (specifically the circled area of the shutter 105). A shutter spring 109 is also loaded as the first actuator 94 is moved through the forward stroke. Unlike the pump return spring 95, the shutter spring 109 is locked in the loaded position of FIG. 26. The position sensor 110 (which may be an optical, electromagnetic, electrical or mechanical sensor) determines when the shutter 105 is in the firing position in which the aperture 107 is aligned with the fluid openings 6. For example, the sensor 110 may be an optical sensor coupled to the control unit 11 (and the reusable second housing) which senses a marker on the shutter. Fluid ejection is prevented when the position sensor determines that the shutter 105 is blocking (or will block very soon) delivery of fluid. The fluid is delivered upon actuation of a second actuator 106 (which may be a firing or dose button 108) which is unlocked when the shutter 105 is in the position of FIG. 26 and the device is ready for delivery of the fluid. In use as described below, the firing button 108 mechanically releases the shutter 105 and the fluid ejector is activated by the control system 11 while the aperture in the shutter 105 is aligned with openings 6 in the vibrating element 4 as determined by the position sensor 110.

Figure 4:
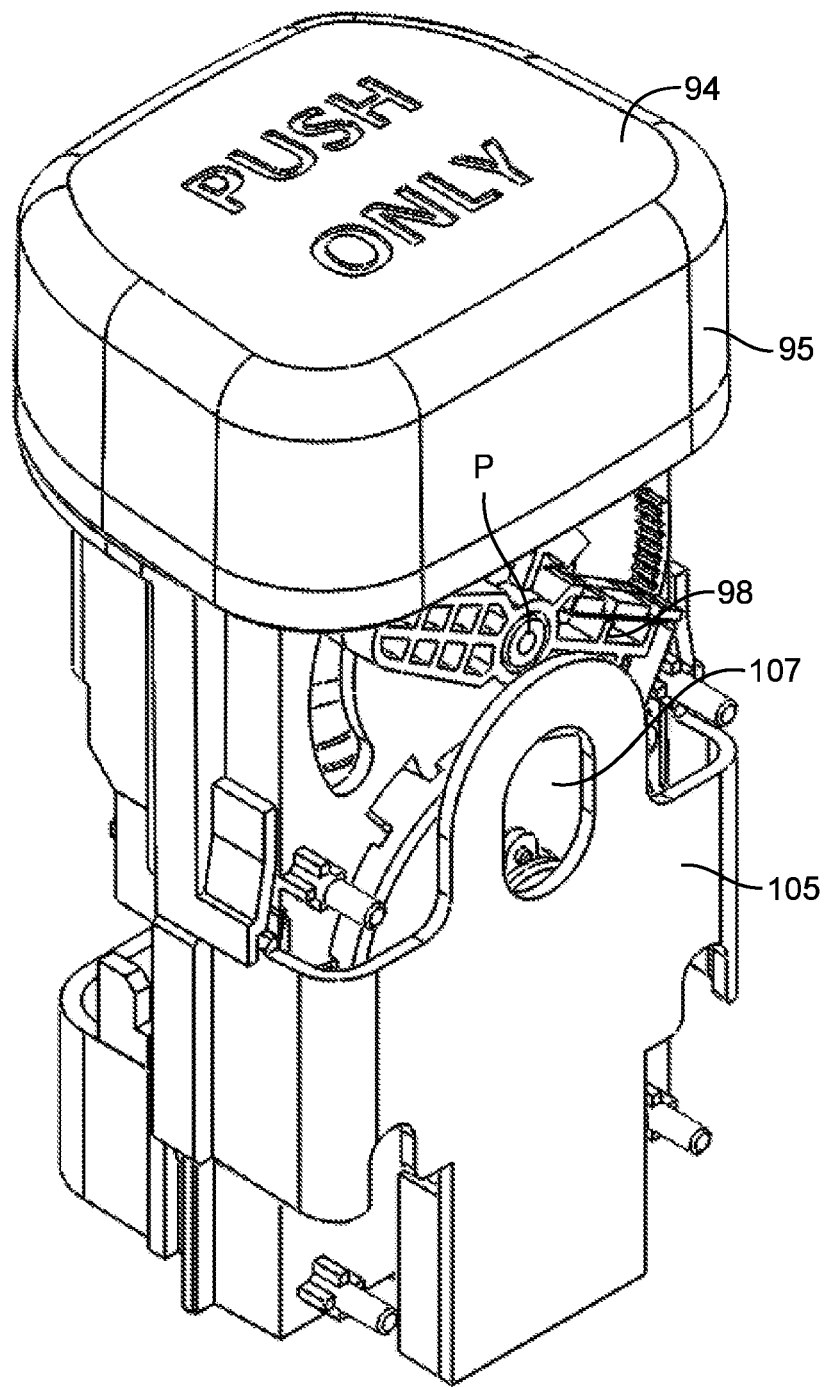
FIG. 4 shows a first housing part with an outer cover removed to show a shutter with an aperture through which the fluid is dispensed.
Figure 18:
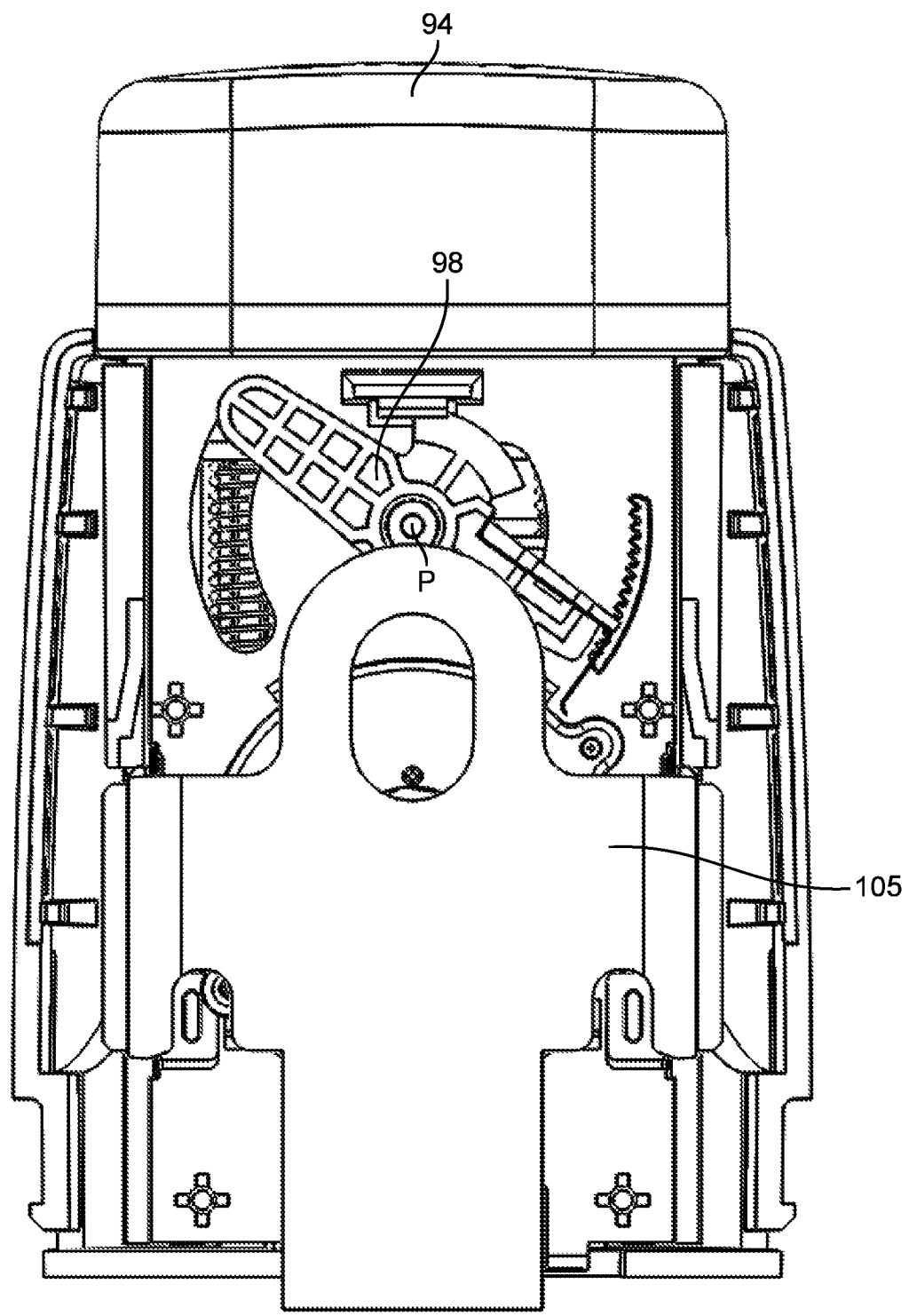
FIG. 18 shows a front view with the shutter in a stored position.
Figure 19:
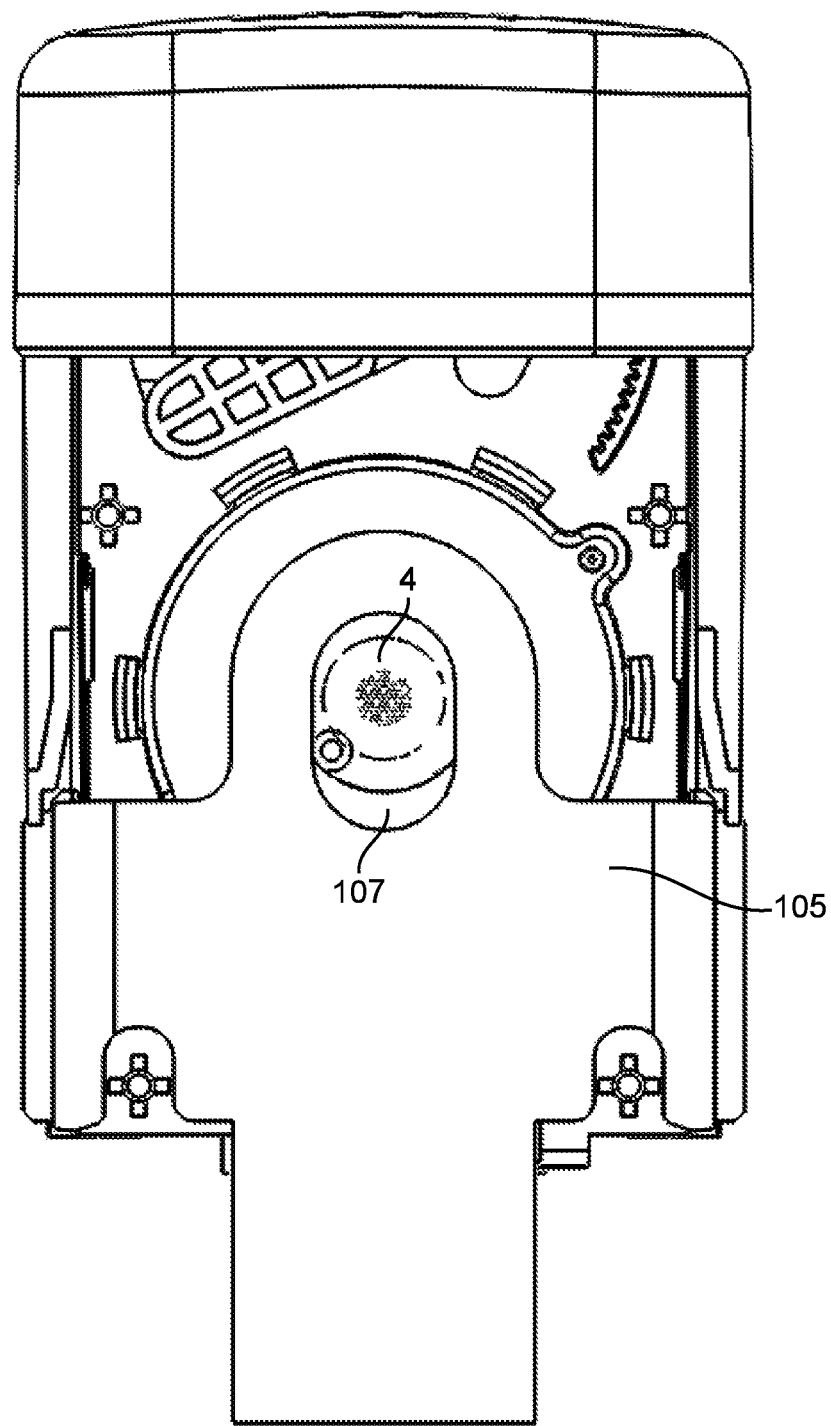
FIG. 19 shows a front view with the shutter in a ready position.
Figure 20:
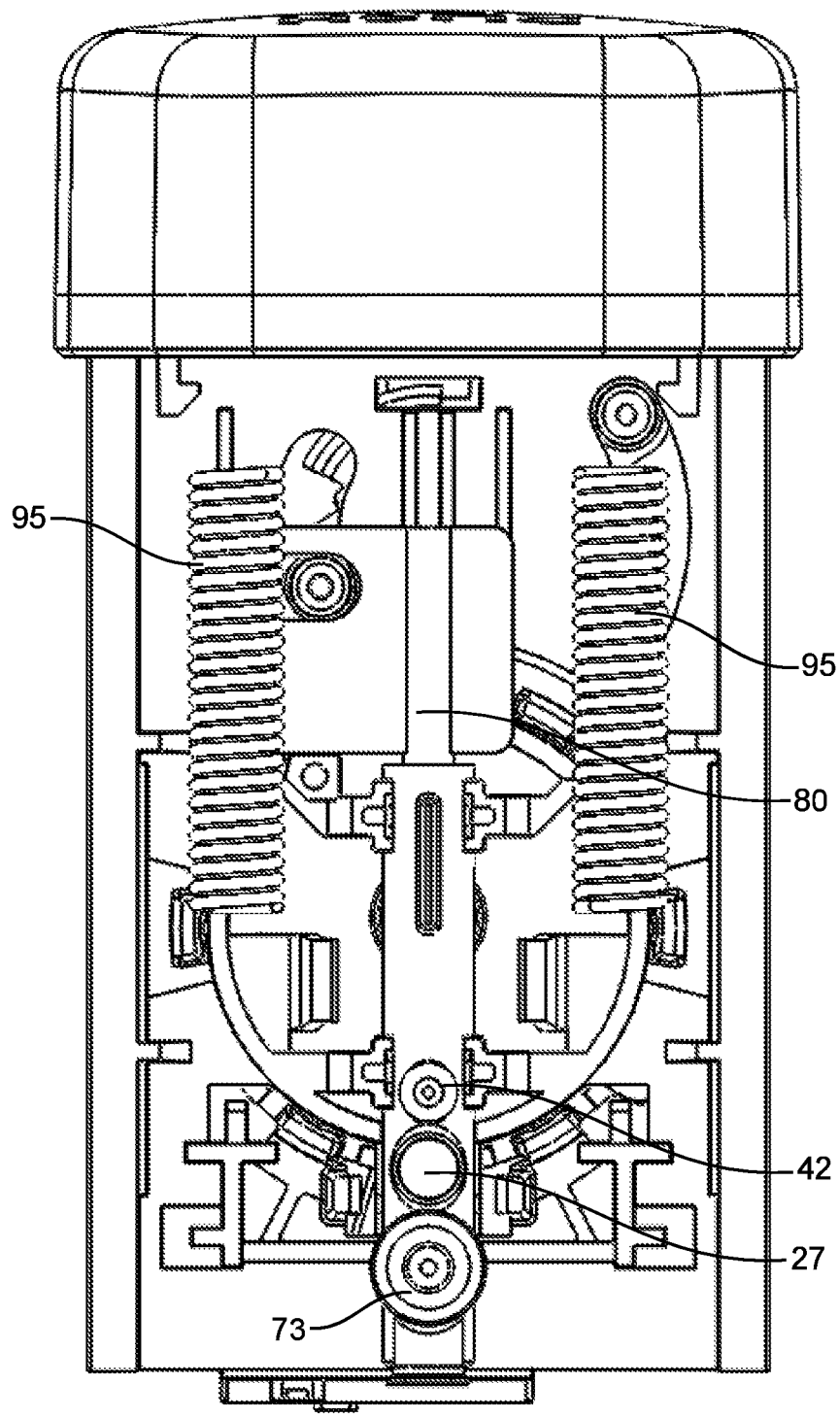
FIG. 20 shows a rear view of the device with the pump in a stored position.
Figure 21:
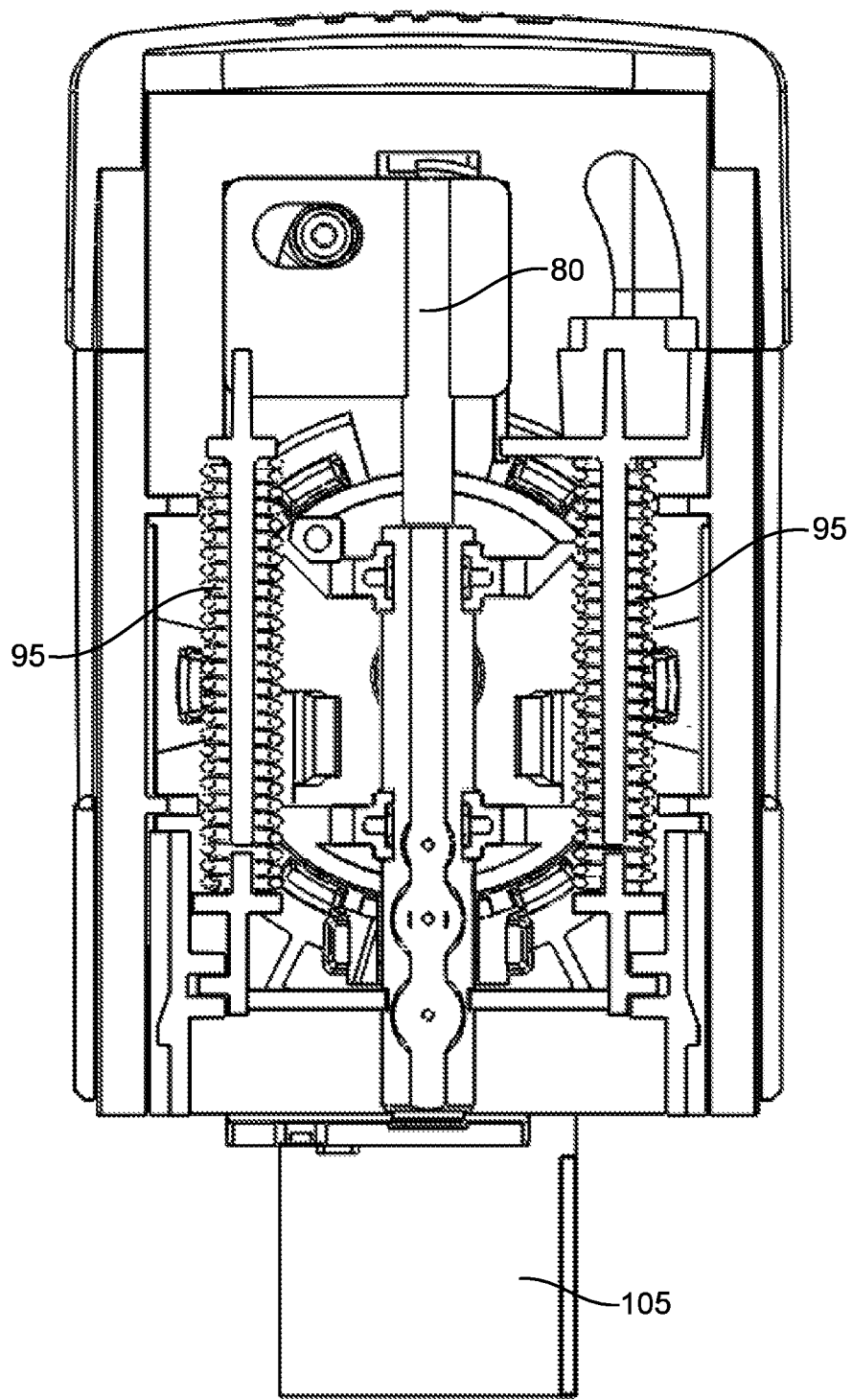
FIG. 21 shows a rear view of the device with the pump in the full forward stroke position.
Figure 23:
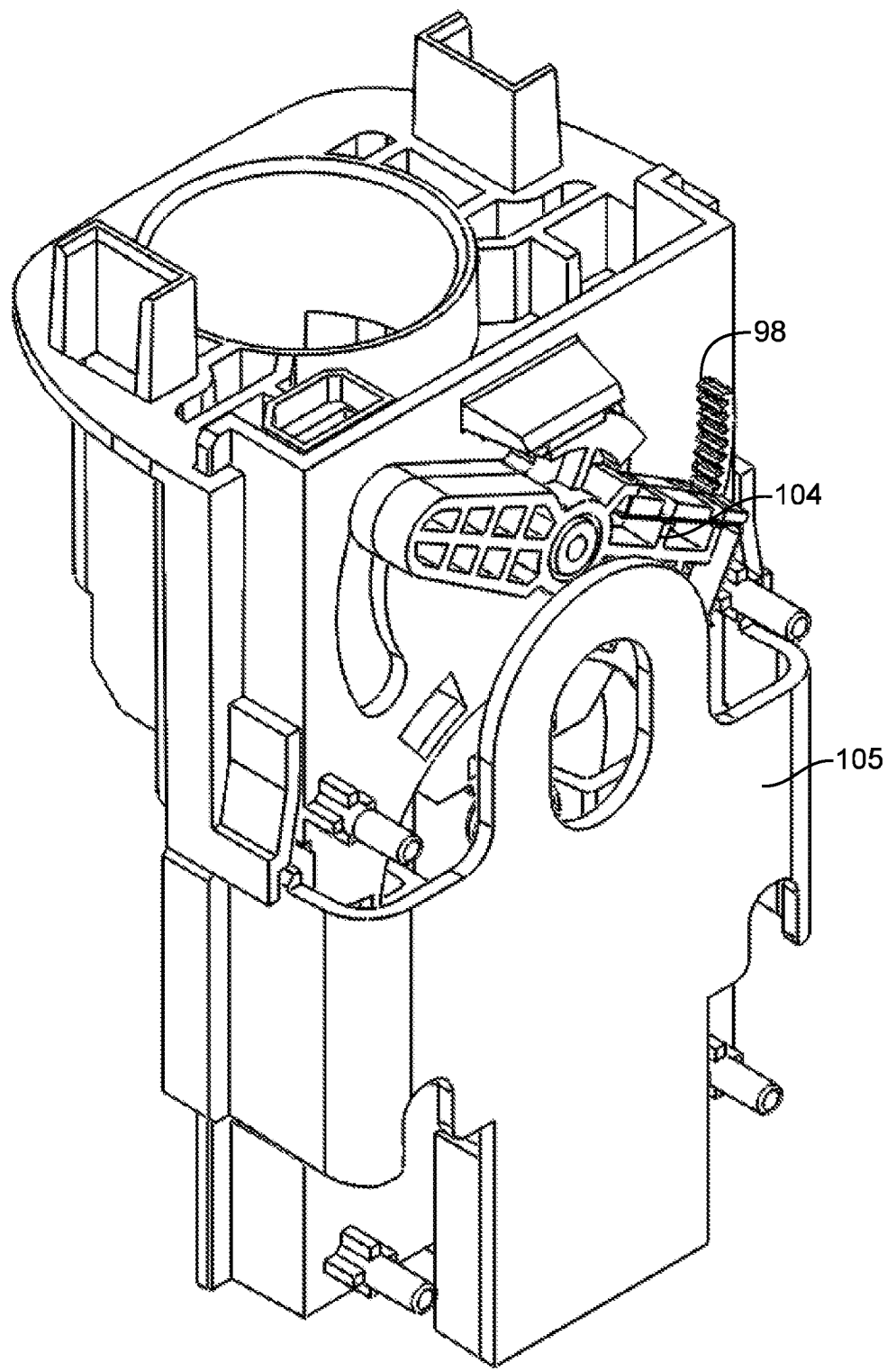
FIG. 23 shows a perspective view with the cap and outer cover removed.
Figure 24:
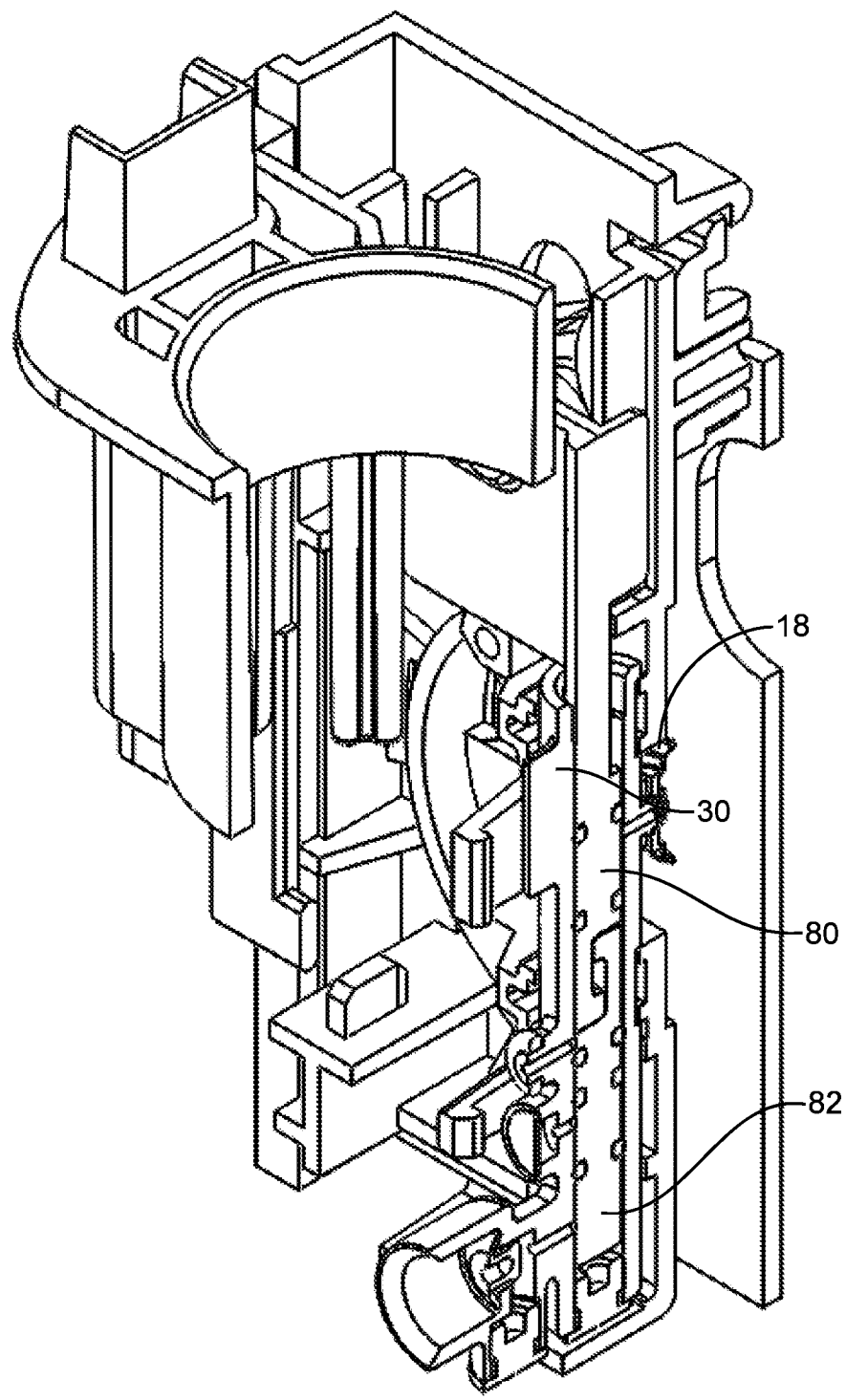
FIG. 24 shows a perspective cross-sectional view of the fluid delivery path and shutter.
Figure 25:
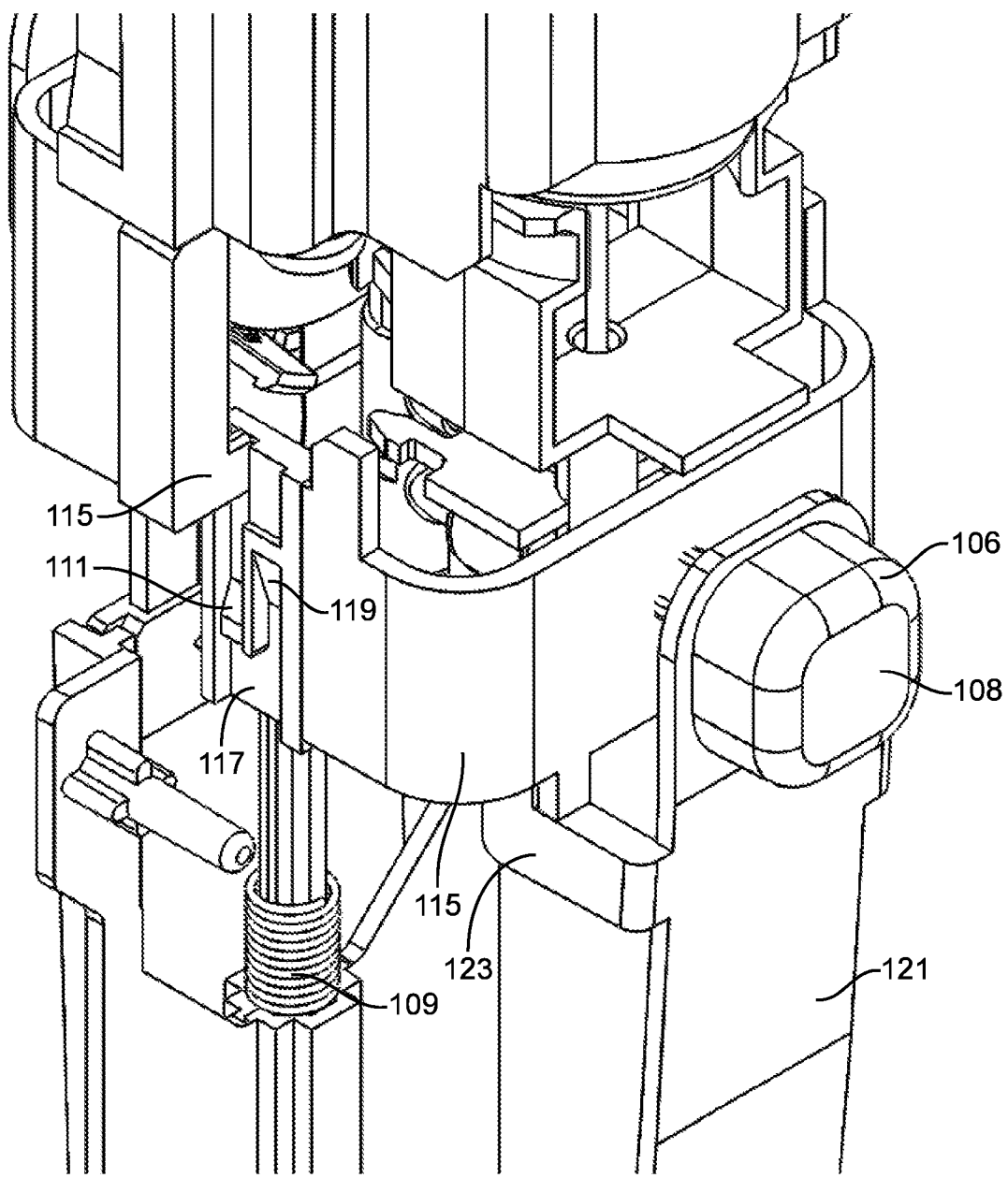
FIG. 25 shows the shutter mechanism and a firing button in a stored position.
Figure 26:
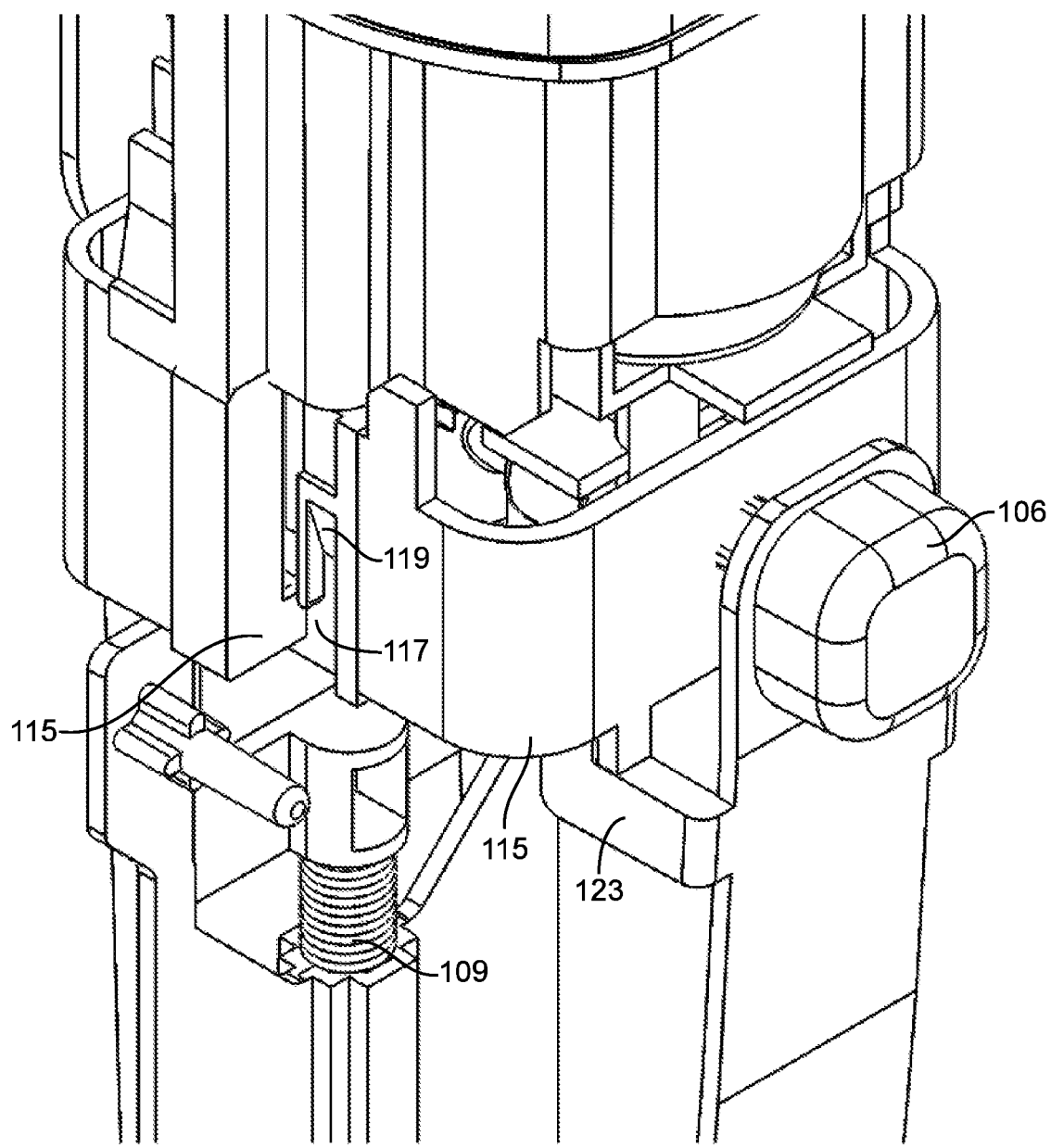
FIG. 26 shows the shutter in a ready state with the shutter spring loaded.

The shutter 105 motion is now described in more detail. Referring to FIGS. 4, 18 and 23, the shutter 105 is in the stored position. The shutter 105 is moved downward by the first actuator 94 so that a tab 109 slides downwardly in a slot 111 and is locked in a ready state of FIGS. 19 and 26. The device is now in an "on" state by activation of a switch (not shown) when the dose is loaded. During the shutter locked state, another sensor (not shown) may determine the device has loaded fluid and is ready to dispense a dose. Activation of the dose button 108 and the subsequent activation and deactivation in accordance with the position sensor's 110 determination of the shutter 105 position is the mechanism by which the dose/ejection is triggered and terminated. Of course, numerous other methods of timing delivery may be used and, furthermore, the fluid may be delivered in a manner independent of the shutter 105 operation.

Figure 27:
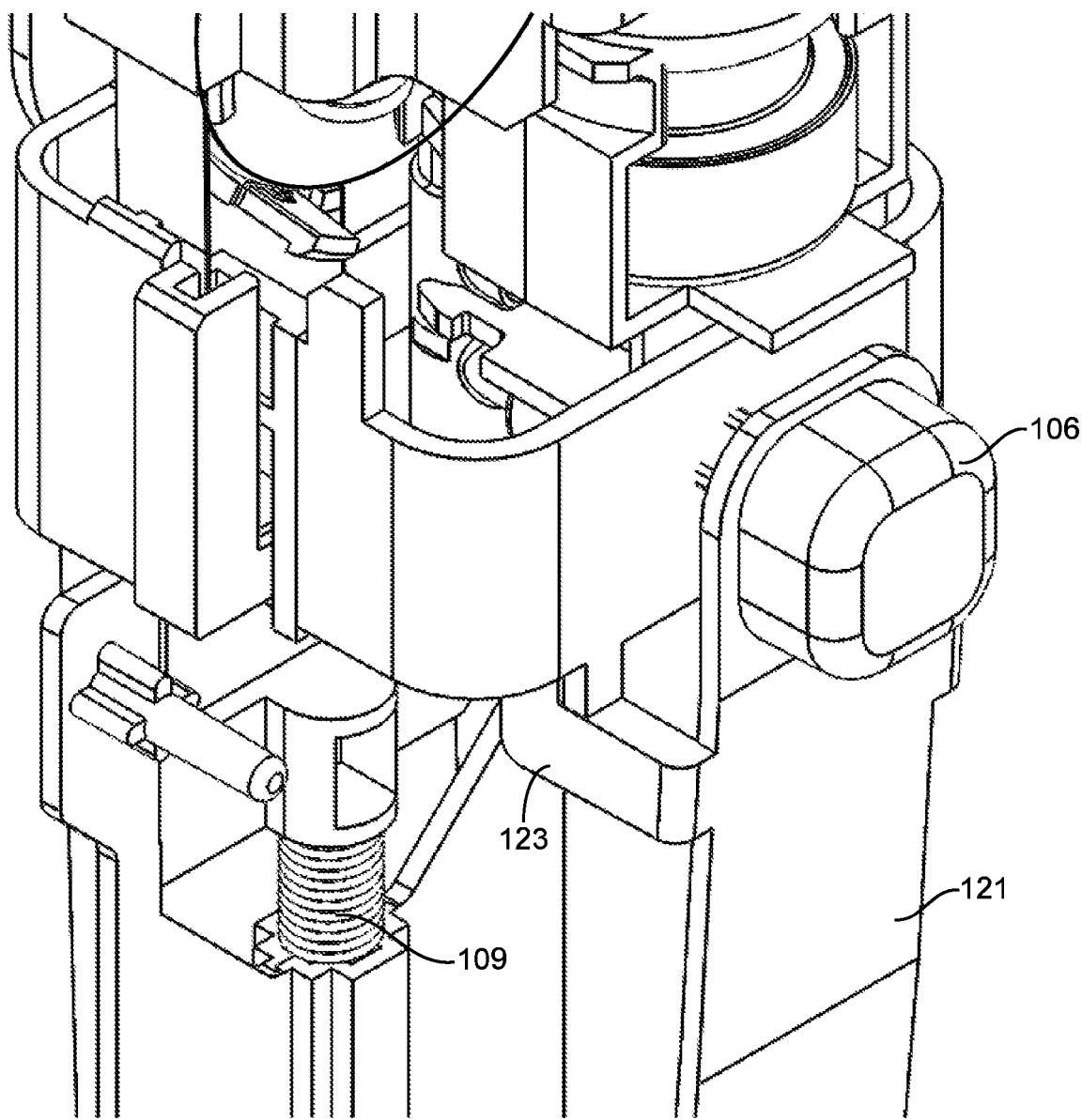
FIG. 27 shows actuation of the firing button which releases the shutter.
Figure 28:
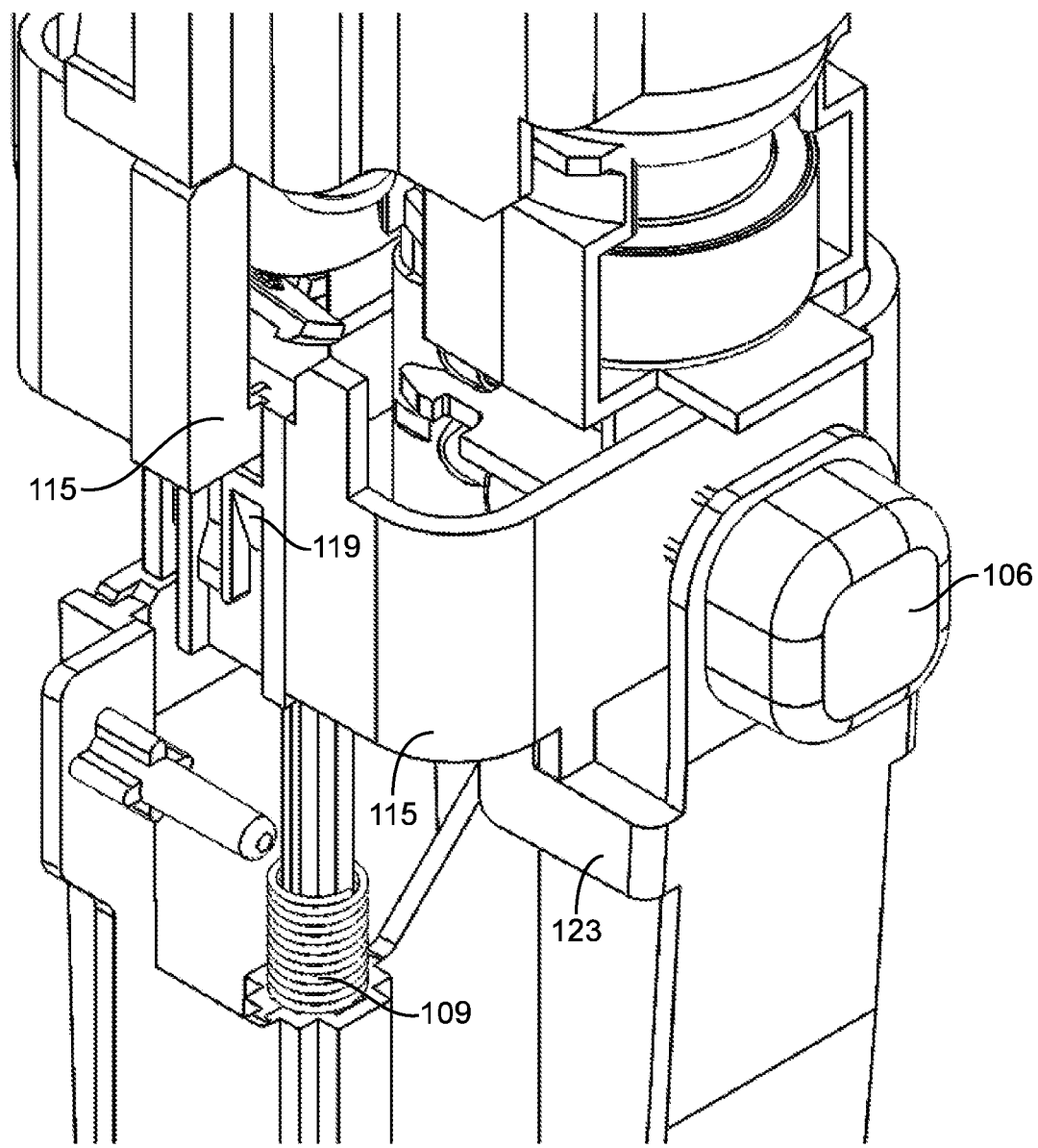
FIG. 28 shows the shutter displaced upwardly by the pump spring at the end of the fluid delivery.
Figure 29:
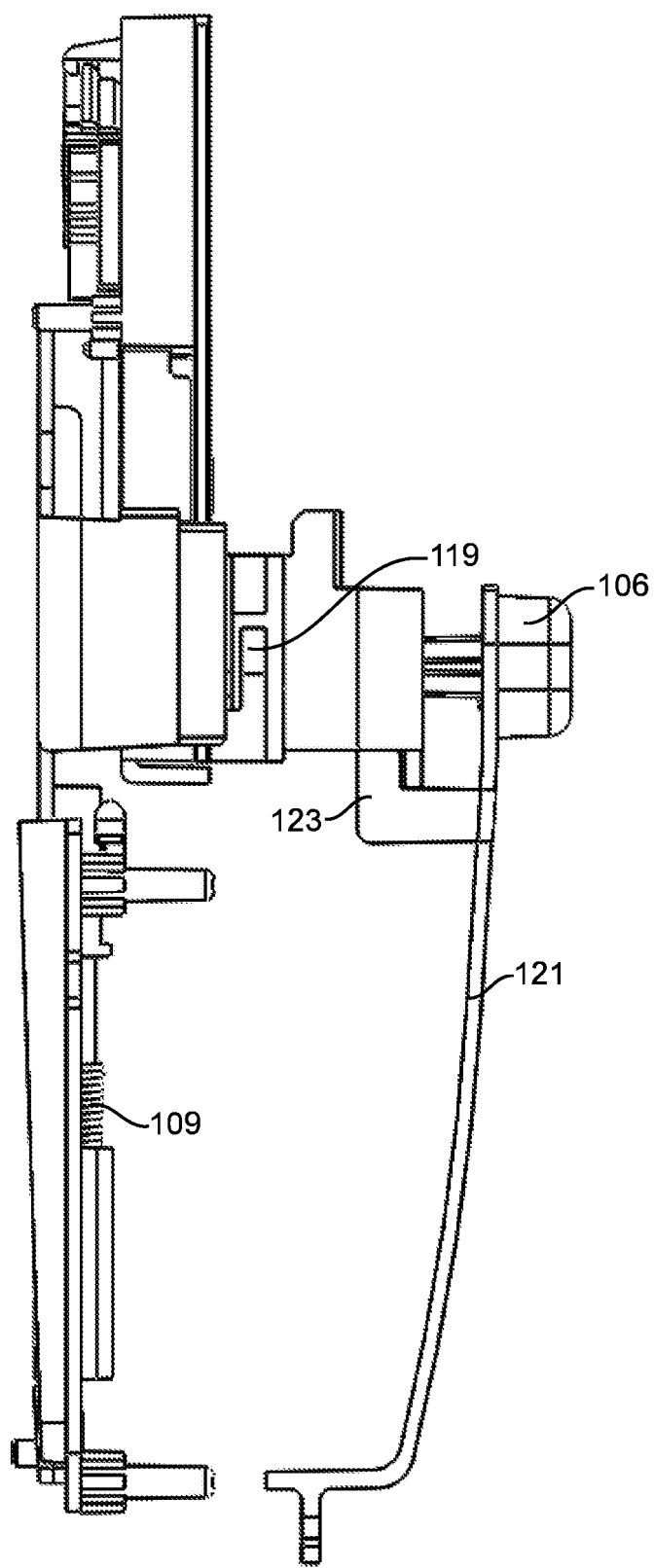
FIG. 29 shows a partial cross-section of the device showing the shutter mechanism.
Figure 30:
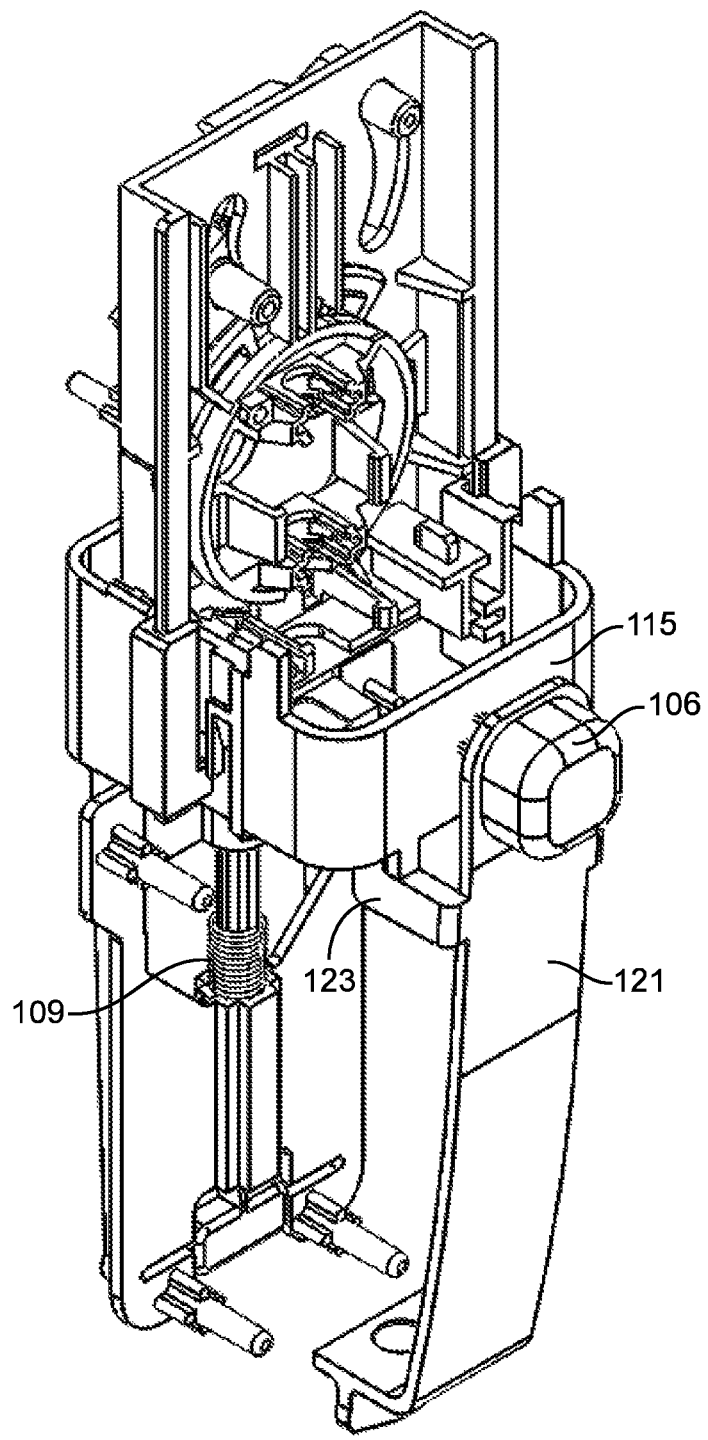
FIG. 30 shows a perspective view of FIG. 29.
Figure 31:
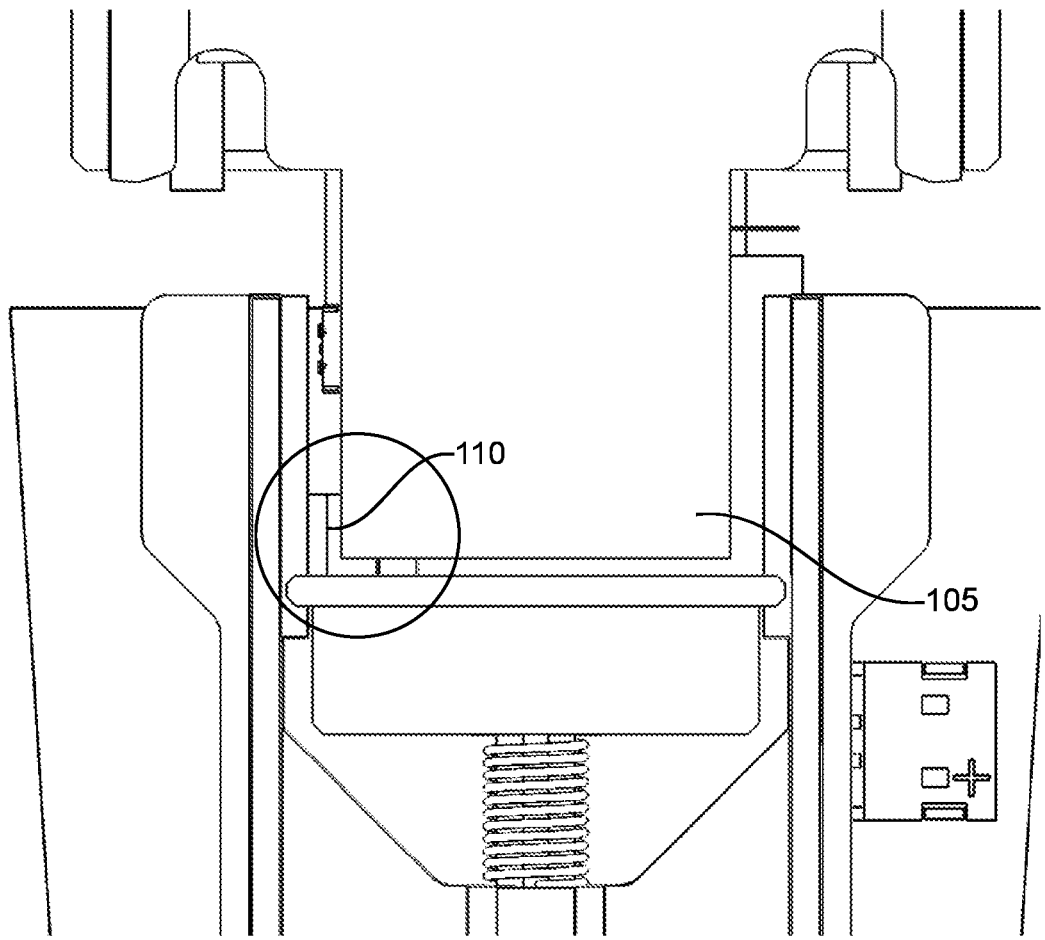
FIG. 31 shows the shutter in the ready state and a sensor which prevents delivery of fluid when the shutter is blocking fluid delivery.
Figure 32:
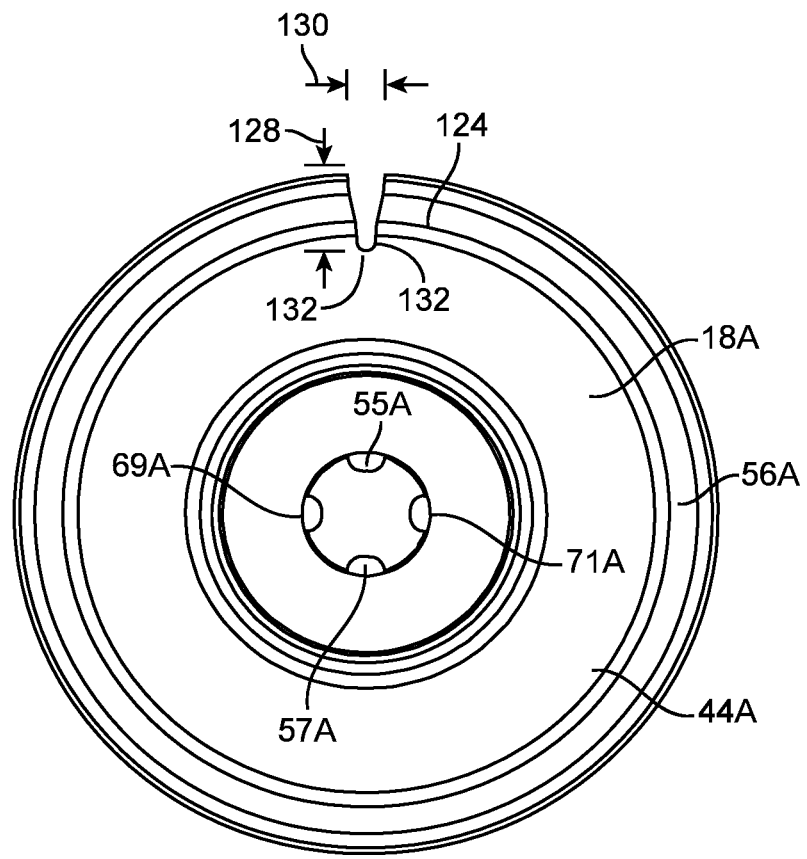
FIG. 32 shows a plan view of another enclosure having a wedge-shaped wall opening.
Figure 33:
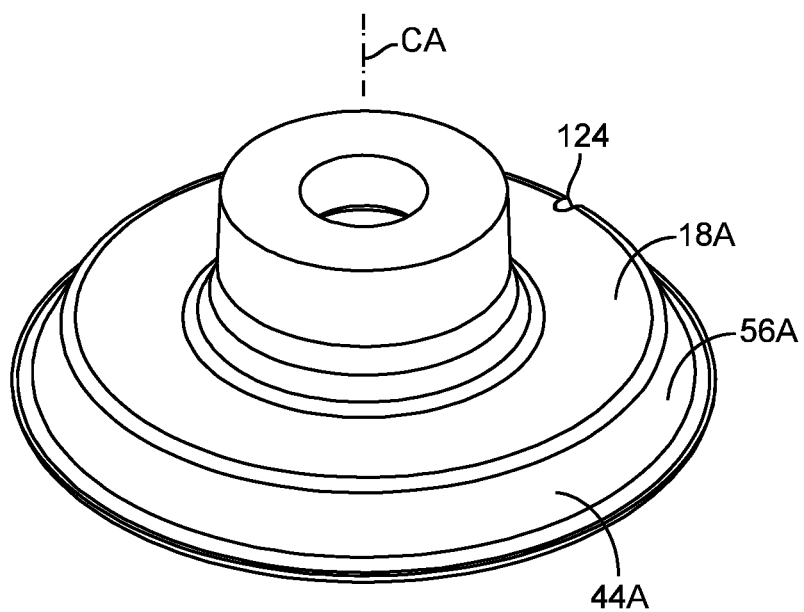
FIG. 33 is a perspective view of the enclosure of FIG. 32.
Figure 34:
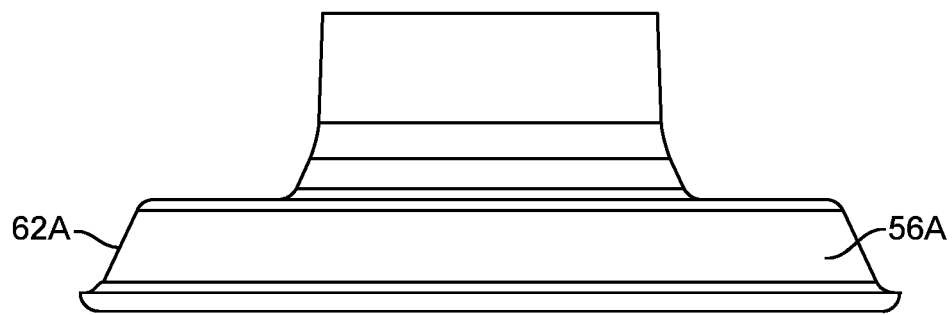
FIG. 34 is a side view of the enclosure of FIGS. 32-33.
Figure 35:
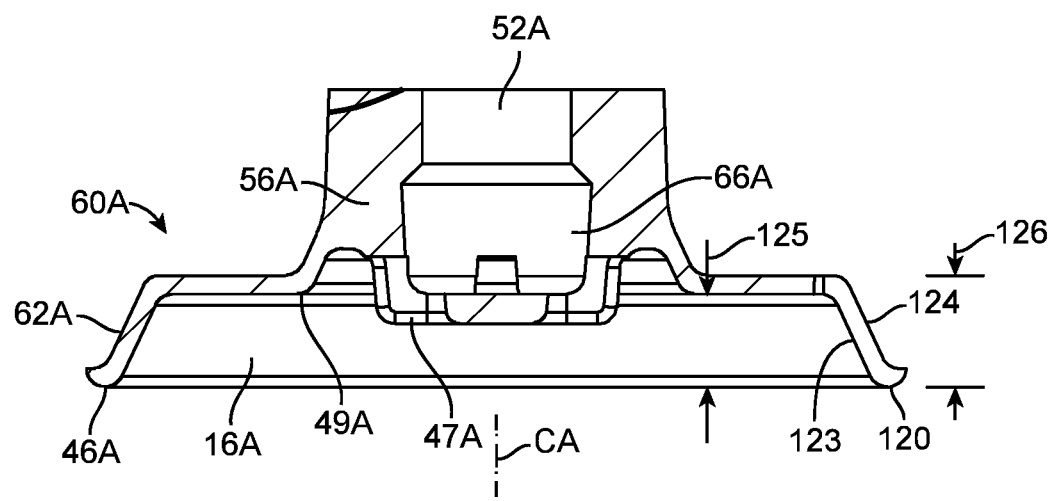
FIG. 35 is a cross-sectional view of the enclosure of FIG. 34.

A shutter lock 115 is displaced by the firing button 108 to the position of FIG. 27 so that the tab 109 on the shutter 105 moves upward in a release slot 117 having a ramp 119. The firing button 108 is mounted to a resilient arm 121 having a pair of hooks 123 which engage the shutter lock 115 and pulls the shutter lock 115 back to the stored position in part due to the resilient nature of the arm 121. A button return spring 125 (see FIG. 17) is compressed upon actuation and returns the button 108 to the ready state and may also serve to return the shutter lock 115 to the stored position.

Use of the device to handle and deliver a dose of the fluid is now described. The fluid container 17 may be mounted prior to use or may be pre-loaded or loaded from a prior use. When loading the fluid container 17 for the first (and optionally only) time, the fluid container 17 is mounted in a cavity 92 and the button is placed over the fluid container 17. The user then depresses the first actuator 94 to force the container 17 downward so that the vent needle 40 and the delivery needle 34 pierce the fluid container as shown in FIG. 7. The fluid container 17 may be locked to prevent removal and replacement of the fluid container 17. The device may be stored in this condition.

Immediately before deciding to deliver the dose, the fluid is delivered to the chamber 16 by actuating (depressing) the first actuator 94 (cap) which moves the pump 32 through a full cycle to load the fluid in the chamber 16. Once the actuator 94 has returned to the default position, the fluid is contained in the chamber 16 and ready for delivery. The first actuator 94 may be any suitable actuator such as the button 95, a lever, a slider, a twist knob or any other suitable mechanical or electro-mechanical actuator without departing from numerous aspects of the present invention. Of course, the fluid may be delivered to the chamber 16 during delivery of the fluid to the eye or immediately before and in a continuous process without departing from virtually all aspects of the present invention. After delivery of the fluid to the chamber 16, the device may also clear the tube 56 of fluid. For example, the pump 32 may draw a volume of displacing medium and deliver the displacing medium into the tube 56 to displace any fluid in the tube 56 into the enclosure 18 prior to delivery.

When the user is ready, the user then actuates the firing button 108 to deliver the fluid to the eye. To aim and align the device, the user positions the device adjacent the eye and looks into the device through the aperture 107 in the shutter 105 and views the vibrating element 4. A light emitting element 114, such as a light tube 116, illuminates part of the device, such as the vibrating element 4, to visually aim and align the device. Of course, any other suitable aiming/aligning method may be used. Once the device is properly aimed, the firing button 108 is actuated to deliver the fluid to the eye. The second actuation may be with the same actuator or a different actuator such as the firing button 108. Although the present invention has been described with a two-step actuation process the two steps may be combined in a single actuation which delivers the fluid to the chamber 16 then determines an appropriate time to deliver the fluid such as by optically differentiating the eyeball from the eyelid. The device delivers substantially all of the fluid and the device is ready for storage after a single actuation and delivery of a single dose or quantity to the eye.

All aspects of the methods and devices as claimed may be applied to the other methods and devices and such claim combinations are expressly incorporated. Furthermore, combinations of size range, ratio, angular or linear coverage, percentage or any other quantity are expressly incorporated into the claims even if the specific combination has not been previously expressly claimed. For example, the alternative ranges 75%, 95% and "all" are used to describe various values which may be used or substituted for one in combination with the other quantities. The terms "first" and "second" shall be interchangeable in the claims since they are not used as terms of natural order but merely to distinguish one from the other. In addition, the claim terms "have" "having" "includes" "including" "comprises" and "comprising" (and all other forms of these terms such as "has") are all open ended as used herein in that "A has B" or "A includes B" means A includes B but may also include other elements or method limitations. Finally, the present invention has been described with reference to some aspects, advantages or operating conditions which are difficult to quantify and directly due to the small volume and fast delivery time. Thus, direct observation and measurement are at times not feasible, however, qualitative information supports some of the assertions. For example, it has been observed that water at the interface of the lip 46 and vibrating element 4 outside the enclosure 18 is drawn into the enclosure 18 when fluid is ejected indicating that air may likely be admitted as well. Furthermore, the fluid is smoothly ejected even with no dedicated vent opening.

The present invention has been described with reference to preferred embodiments, however, various modifications may be made without departing from the features and aspects of the invention. For example, the pump 32 may be a syringe, the enclosure 18 may be a rigid dome or the enclosure 18 may be attached to the vibrating element 4 without departing from aspects of the invention.

What is claimed:

1. A device for delivering a volume of fluid to an eye, comprising:
    a housing;
    a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;
    an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed; and a pump having a first part and a second part, the first part reciprocates between a stored position to a forward stroke position at a greatest displacement and back from the forward stroke position to the stored position each cycle, the pump also having a second pump part which also reciprocates between a stored position to a forward stroke position at a maximum displacement and back to the stored position each cycle.

2. The device of claim 1, wherein the pump has an outlet fluidly coupled to the chamber formed by the enclosure and the vibrating element; and a first actuator operably coupled to the pump, wherein actuation of the first actuator activates the pump to deliver the volume of fluid to the chamber.

3. The device of claim 1, further comprising a second actuator operably coupled to the vibrating element, wherein actuation of the second actuator causes the vibrating element to vibrate and eject the fluid through the plurality of openings.

4. The device of claim 1, wherein the chamber defined by the enclosure is configured to hold a maximum liquid volume of 10-14 microliters.

5. The device of claim 1, wherein the lip is spaced apart from the fluid side of the vibrating element by less than 150 microns.

6. The device of claim 1, wherein the lip is spaced apart from the fluid side of the vibrating element by less than 250 microns about an angle of at least 270 degrees when viewed along the central axis.

7. The device of claim 1, wherein the enclosure has an internal surface that is configured to be in contact with the volume of fluid, the internal surface of the enclosure forms the chamber with the vibrating element, the internal surface being shaped so that at least 75% of the internal surface, when in contact with the volume of fluid, is no more than 0.040 inch from a nearest of the plurality of openings.

8. The device of claim 1, further comprising a piezoelectric element coupled to the vibrating element.

9. The device of claim 1, wherein the vibrating element has a maximum amplitude which is less than an average separation distance between the lip and the vibrating element.

10. The device of claim 1, wherein the vibrating element has a thickness measured from the fluid side to the delivery side of 100-180 microns.

11. The device of claim 1, wherein the lip is in contact with the vibrating element around at least 270 degrees of the plurality of openings when viewed along the central axis, to hold the fluid in the enclosure.

12. The device of claim 1, wherein the lip has no direct attachments to the vibrating element.

13. The device of claim 1, wherein the lip is made of a resilient material having a durometer of less than Shore 60a.

14. The device of claim 1, wherein the lip is biased against the vibrating element in the direction of the central axis of the vibrating element.

15. The device of claim 1, wherein the lip exerts a force of no more than 3 gram-f on the vibrating element measured in the direction of the central axis of the vibrating element.

16. The device of claim 1, further comprising a mechanism for biasing the lip against the vibrating element.

17. The device of claim 1, wherein the lip and the vibrating element are adjacent one another to prevent fluid from passing therebetween along a closed loop which encircles the plurality of openings.

18. The device of claim 1, wherein the lip is spaced apart from the vibrating element by a separation distance of at least 125 microns around at least 270 degrees of the plurality of openings when viewed along the central axis of the vibrating element.

19. The device of claim 1, wherein the enclosure does not include a vent opening to vent air into the enclosure when the fluid is ejected through the plurality of openings other than between the lip and the vibrating element and through at least some of the plurality of openings.

20. The device of claim 1, further comprising:

a fluid container fluidly coupled to the chamber of the enclosure, the fluid container having a fluid carrying capacity which is at least 150 times a volume of the enclosure; and wherein the pump is configured to deliver one dose size only.

21. The device of claim 1, wherein the vibrating element defines an enclosed border positioned adjacent to a surface of the lip, the enclosed border defining an enclosed feed area bounded by the enclosed border, the plurality of openings in the vibrating element encompassing and defining a delivery area of the vibrating element.

22. The device of claim 1, wherein the enclosure has a sidewall and a main inlet that is configured to receive the volume of fluid to be dispensed, the enclosure also having a first inlet and a second inlet through which the volume of fluid to be dispensed enters the chamber, the first inlet and the second inlet leading to the chamber and both oriented to direct the volume of fluid to be dispensed at the sidewall of the enclosure before being directed at the plurality of openings.

23. The device of claim 22, wherein the first inlet and the second inlet direct at least 90% of fluid at the enclosure and less than 10% of fluid is directed at the vibrating element before being directed at the enclosure.

24. The device of claim 1, further comprising:

a tube having a lumen; and the enclosure having a main inlet fluidly coupled to the lumen in the tube, the main inlet being oriented to direct the fluid at an inner wall of the enclosure which forms a flow splitting chamber, the flow splitting chamber having at least two separate inlets leading to the chamber and each inlet to the chamber directing the fluid at a sidewall of the enclosure.

25. The device of claim 24, wherein the flow splitting chamber further comprising a third inlet and a fourth inlet corresponding to a third flow path and a fourth flow path, respectively.

26. The device of claim 1, wherein the central axis of the vibrating element is defined by a central orientation of a spray pattern emitted by the plurality of openings; and the enclosure has a main inlet which directs the flow in a direction within 30 degrees of the central axis, the enclosure having a sidewall and a flow splitting chamber fluidly coupled to the main inlet to receive the fluid, the flow splitting chamber having a shape which redirects and splits a fluid flow from the main inlet to at least a first inlet and a second inlet oriented 60-90 degrees from the central axis, the first inlet and the second inlet being directed at the sidewall of the enclosure before the fluid is directed to the plurality of openings.

27. The device of claim 1, further comprising:

a tube having a lumen with a volume of less than 2 microliters;

a valve having an open position which permits fluid flow through the lumen and a closed position which prevents fluid flow through the lumen; and the enclosure having a main inlet fluidly coupled to the lumen in the tube.

28. The device of claim 1, wherein the first part of the pump has an extension which extends toward the second part, the second part also having an extension which extends toward the first part and interlocks with the extension of the first part, the first part driving the second part through the cycle.

29. The device of claim 1, further comprising a first actuator operably coupled to the first part, the actuator driving the first part through the forward stroke and also loading a pump return spring during the forward stroke, the pump return spring when loaded moves the first part and the second part back to the stored position from the forward stroke position.

30. The device of claim 1, wherein the volume of fluid to be dispensed is drawn into a cavity formed between the first and second parts during the forward stroke of the first part.

31. The device of claim 1, wherein the volume of fluid to be dispensed is drawn into a cavity during the forward stroke, the cavity being formed between the first part and the second part, a size of the cavity changing as the first and second parts move toward and away from one another.

32. The device of claim 1, wherein the pump has a cavity which holds a volume of fluid of 7-12 microliters which is delivered to the enclosure during use.

33. The device of claim 1, further comprising:
a tube having a lumen fluidly coupled to the chamber; and
a valve which is opened to permit fluid flow through the lumen and closed to block fluid flow through the lumen, a total downstream volume is defined by a total volume including at least the lumen and the tube which is downstream of the valve, a volume of fluid delivered to the chamber may be 40%-70% of the total downstream volume.

34. The device of claim 1, further comprising an air make-up chamber coupled to the pump, the pump forcing air from the air make-up chamber into a fluid container during each cycle.

35. The device of claim 34, wherein the pump draws air into the air make-up chamber during a forward stroke of the first part and forces air into the fluid container during a return stroke of the first part.

36. The device of claim 2 further comprising:
a shutter having an aperture, the shutter being movable from the stored position, which covers the plurality of openings when viewed along the central axis of the vibrating element, to a delivery position in which the plurality of openings are exposed when viewed along the central axis through the aperture of the shutter; and
a shutter spring coupled to the shutter, the shutter spring being loaded when the first actuator moves the first part of the pump during a forward stroke, the shutter spring being coupled to the shutter which is moved from the delivery position back to the stored position by the shutter spring.

37. The device of claim 1, further comprising a control system mounted to the housing, the control system being coupled to a first actuator and being operably coupled to the vibrating element to control the vibrating element.

38. The device of claim 37, wherein the housing includes a first housing part and a second housing part, the first housing part being removably coupled to the second housing part; the control system being mounted to the first housing part.

39. The device of claim 1, wherein: the lip has a PTFE coating adjacent to the vibrating element to reduce friction therebetween, the coating extending around at least 270 degrees of the lip when viewed along the central axis of the vibrating element.

40. The device of claim 1, wherein: the vibrating element has a PTFE coating adjacent to the lip to reduce friction therebetween, the coating extending around at least 270 degrees when viewed along the central axis of the vibrating element.

41. The device of claim 1, wherein: an inner surface of the enclosure is hydrophobic over at least 70% of the inner surface in contact with fluid.

42. The device of claim 1, further comprising: a wall opening extending through the wall to expose the chamber.

43. The device of claim 42, wherein: the wall opening forms a gap in the lip.

44. The device of claim 42, wherein: the wall opening has a longitudinal dimension measured from the lip in the direction of the central axis of the vibrating element and a radial dimension measured in a radial direction relative to the central axis, the enclosure having an internal wall with a side facing the plurality of openings in the vibrating element which is spaced apart from the openings by a separation.

45. The device of claim 42, wherein: the wall includes a frustoconical portion, the wall opening extending proximally from the lip for at least 80% of a length of the frustoconical portion.

46. The device of claim 44, wherein: the longitudinal dimension of the wall opening is at least 80% of the separation between the vibrating element and the side of the enclosure facing the plurality of openings.

47. A method of delivering a volume of fluid to an eye, comprising:
delivering a volume of a fluid to the chamber of a device of claim 1 with the pump; and
vibrating the vibrating element so that the fluid in the chamber is ejected through the plurality of openings toward an eye.

48. The method of claim 47, wherein: the delivering is carried out with the volume of the fluid in the chamber to be delivered being 7-12 microliters.

49. A device for delivering a volume of fluid to an eye, comprising:
a housing;
a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;
an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed;

a fluid container fluidly coupled to the chamber of the enclosure, the fluid container having a fluid carrying capacity which is at least 150 times the volume of the enclosure; and a pump which is configured to deliver one dose size only.

50. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;

an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed; and an air make-up chamber coupled to a pump, the pump forcing air from the make-up chamber into a fluid container during each cycle.

51. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;

an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed, and wherein the enclosure has a sidewall and a main inlet which receives the volume of fluid to be dispensed, the enclosure also having a first inlet and a second inlet through which the volume of fluid to be dispensed enters the chamber, the first inlet and the second inlet leading to the chamber and both oriented to direct the volume of fluid to be dispensed at the sidewall of the enclosure before being directed at the plurality of openings.

52. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;

an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed; and a tube having a lumen, wherein the enclosure has a main inlet fluidly coupled to the lumen in the tube, the main inlet being oriented to direct the fluid at an inner wall of the enclosure which forms a flow splitting chamber, the flow splitting chamber having at least two separate inlets leading to the chamber and each inlet to the chamber directing the fluid at a sidewall of the enclosure.

53. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated, wherein the central axis of the vibrating element is defined by a central orientation of a spray pattern emitted by the plurality of openings; and an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed, wherein the enclosure has a main inlet which directs the flow in a direction within 30 degrees of the central axis, the enclosure having a sidewall and a flow splitting chamber fluidly coupled to the main inlet to receive the fluid, the flow splitting chamber having a shape which redirects and splits a fluid flow from the main inlet to at least a first inlet and a second inlet oriented 60-90 degrees from the central axis, the first inlet and the second inlet being directed at the sidewall of the enclosure before the fluid is directed to the plurality of openings.

54. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;

an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed; and a wall opening extending through the wall to expose the chamber, the wall opening forming a gap in the lip.

55. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated;

an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed; and a wall opening extending through the wall to expose the chamber, wherein the wall includes a frustoconical portion and the wall opening extends proximally from the lip for at least 80% of a length of the frustoconical portion.

56. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated; and an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed, wherein the enclosure has an internal surface that is configured to be in contact with the volume of fluid, the internal surface of the enclosure forms the chamber with the vibrating element, the internal surface being shaped so that at least 75% of the internal surface, when in contact with the volume of fluid is no more than 0.040 inch from a nearest of the plurality of openings.

57. A device for delivering a volume of fluid to an eye, comprising:

a housing;

a fluid ejector located within the housing, the fluid ejector having a vibrating element with a plurality of openings and a central axis, the vibrating element having a fluid side and a delivery side with the plurality of openings extending from the fluid side to the delivery side, the fluid ejector ejecting fluid from the fluid side through the plurality of openings to the delivery side when the vibrating element is vibrated; and an enclosure positioned adjacent the fluid side the vibrating element, the enclosure and the vibrating element forming a chamber, wherein the enclosure includes a wall having a lip positioned adjacent the fluid side of the vibrating element, the lip extending around the plurality of openings, the enclosure and the vibrating element together defining the chamber which holds a volume of the fluid to be dispensed, a tube having a lumen fluidly coupled to the chamber; and a valve which is opened to permit fluid flow through the lumen and closed to block fluid flow through the lumen, a total downstream volume is defined by a total volume including at least the lumen and the tube which is downstream of the valve, a volume of fluid delivered to the chamber may be 40%-70% of the total downstream volume.

* * * * *